US011149243B2

(12) United States Patent
Jeon et al.

(10) Patent No.: US 11,149,243 B2
(45) Date of Patent: Oct. 19, 2021

(54) ELECTRONIC DEVICE, WEARABLE DEVICE, AND METHOD OF PROVIDING CONTENT-BASED SOMATIC SENSES USING ULTRASOUND

(71) Applicant: SAMSUNG ELECTRONICS CO., LTD., Suwon-si (KR)

(72) Inventors: Seung-ryong Jeon, Incheon (KR); Ki-hyun Kim, Suwon-si (KR); Taek-soo Kim, Yongin-si (KR); Eun-jung Lee, Seongnam-si (KR); Gyeong-cheol Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 366 days.

(21) Appl. No.: 15/647,370

(22) Filed: Jul. 12, 2017

(65) Prior Publication Data
US 2018/0135001 A1  May 17, 2018

Related U.S. Application Data

(60) Provisional application No. 62/421,417, filed on Nov. 14, 2016.

(30) Foreign Application Priority Data

Feb. 20, 2017 (KR) .................. 10-2017-0022464

(51) Int. Cl.
*H04M 1/72403* (2021.01)
*C12M 1/00* (2006.01)
*C12M 3/00* (2006.01)
*C12M 3/06* (2006.01)
*C12M 1/02* (2006.01)

(52) U.S. Cl.
CPC .............. *C12M 23/58* (2013.01); *C12M 1/00* (2013.01); *C12M 1/02* (2013.01); *C12M 3/00* (2013.01); *C12M 3/06* (2013.01); *C12M 23/02* (2013.01); *C12M 23/34* (2013.01); *C12M 23/44* (2013.01); *C12M 27/00* (2013.01); *H04M 1/72403* (2021.01)

(58) Field of Classification Search
CPC .......... C12M 1/00; C12M 1/02; C12M 23/02; C12M 23/34; C12M 23/44; C12M 23/58; C12M 27/00; C12M 3/00; C12M 3/06; H04M 1/72522
See application file for complete search history.

(56) References Cited

U.S. PATENT DOCUMENTS 9,265,974 B2    2/2016  You et al.
9,522,278 B1 *  12/2016 Heldman ............. A61B 5/4082
2014/0211593 A1 * 7/2014  Tyler .................... A61B 5/0476
                                                    367/137

(Continued)

*Primary Examiner* — Beau D Spratt
*Assistant Examiner* — Reji Kartholy
(74) *Attorney, Agent, or Firm* — Sughrue Mion, PLLC

(57) ABSTRACT

Provided is an electronic device for providing somatic senses based on content. The electronic device includes: a processor configured to generate an ultrasound driving signal for evoking somatic senses corresponding to somatosensory data by stimulating a certain region of the brain of a user; and a communication interface configured to transmit the generated ultrasound driving signal to an external device, wherein the somatosensory data corresponds to the content.

17 Claims, 15 Drawing Sheets

(56) References Cited

U.S. PATENT DOCUMENTS

| | | |
|---|---|---|
| 2015/0094585 A1* | 4/2015 | Ter-Ovanesyan ...... A61B 8/468 600/443 |
| 2015/0134031 A1* | 5/2015 | Moffitt ................. A61N 1/0534 607/62 |
| 2015/0251023 A1* | 9/2015 | You .......................... A61N 7/00 601/2 |
| 2015/0251025 A1 | 9/2015 | You et al. |
| 2017/0007853 A1* | 1/2017 | Alford ................. A61B 5/4848 |
| 2017/0113056 A1* | 4/2017 | Stocco .................. A61N 2/006 |
| 2017/0293259 A1* | 10/2017 | Ochiai ................ G03H 1/0005 |

\* cited by examiner

ELECTRONIC DEVICE, WEARABLE DEVICE, AND METHOD OF PROVIDING CONTENT-BASED SOMATIC SENSES USING ULTRASOUND

CROSS-REFERENCE TO RELATED APPLICATIONS

This application claims the benefit of U.S. Provisional Application No. 62/421,417, filed on Nov. 14, 2016, in the U.S. Patent and Trademark Office, and Korean Patent Application No. 10-2017-0022464, filed on Feb. 20, 2017, in the Korean Intellectual Property Office, the disclosures of which are incorporated herein in their entireties by reference.

BACKGROUND

1. Field

The present disclosure relates to an electronic device, a wearable device, and a method of providing content-based somatic senses by using ultrasonic waves, and a non-transitory computer-readable recording medium for storing program code executing the method.

2. Description of the Related Art

There have been attempts to augment a sense of immersion and reality in content by providing users consuming the content with physical effects similar to a subject appearing on the content. For example, to provide a user with a physical effect similar to a subject appearing on the content, limited types of physical stimuli, e.g., vibrations, temperature stimuli, electrical stimuli, etc., have been actually applied to certain body parts of the user.

However, when using the above method, the user has to wear gear such as gloves or a full-length body suit on body parts where the user wants to evoke somatic senses. Thus, according to limitations such as stimulus characteristics of the gear or a mounting location of the gear, types of somatic senses that the user may feel or locations where the somatic senses may be evoked are limited.

SUMMARY

Provided are an electronic device, a wearable device, and a method of providing content-based somatic senses when a user uses content.

Provided are an electronic device, a wearable device, and a method of obtaining somatosensory data corresponding to somatosensory elements included in content.

Provided are an electronic device, a wearable device, and a method of obtaining ultrasound driving signals for evoking somatic senses corresponding to content by reflecting characteristics of content, sensory characteristics of each user, personal preference, etc.

Additional aspects will be set forth in part in the description which follows and, in part, will be apparent from the description, or may be learned by practice of the presented embodiments.

According to an aspect of an exemplary embodiment, an electronic device for providing somatic senses based on content, includes: a processor configured to generate an ultrasound driving signal for evoking somatic senses corresponding to somatosensory data by stimulating a certain region of the brain of a user; and a communication interface configured to transmit the generated ultrasound driving signal to an external device, wherein the somatosensory data corresponds to the content.

According to an aspect of another exemplary embodiment, a method of providing somatic senses based on content, includes: generating an ultrasound driving signal for evoking somatic senses corresponding to somatosensory data by stimulating a certain region of the brain of a user; and transmitting the generated ultrasound driving signal to an external device, wherein the somatosensory data corresponds to the content.

According to an aspect of another exemplary embodiment, a wearable device for providing somatic senses based on content, includes: a processor configured to obtain an ultrasound driving signal for evoking somatic senses corresponding to somatosensory data by stimulating a certain region of the brain of a user; and an ultrasound transducer configured to output an ultrasound signal based on the obtained ultrasound driving signal, wherein the somatosensory data corresponds to the content.

According to an aspect of another exemplary embodiment, there is provided a method of providing, by a wearable device, somatic senses based on content, the method including: obtaining an ultrasound driving signal for evoking somatic senses corresponding to somatosensory data by stimulating a certain region of the brain of a user; and outputting an ultrasound signal to the brain of the user based on the obtained ultrasound driving signal, wherein the somatosensory data corresponds to the content.

The content may comprise somatosensory elements, and the somatosensory data may comprise at least one of types of somatic senses, locations where the somatic senses are evoked, points in time when the somatic senses are evoked, intensities of the somatic senses, and frequencies of the somatic senses corresponding to the somatosensory elements, the somatosensory data being synchronized with the somatosensory elements of the content.

The content may comprise somatosensory elements, and the method may further comprise generating the somatosensory data by analyzing the somatosensory elements.

According to an aspect of another exemplary embodiment, a non-transitory computer-readable recording medium has recorded thereon a program which, when executed by a computer, performs the above methods.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
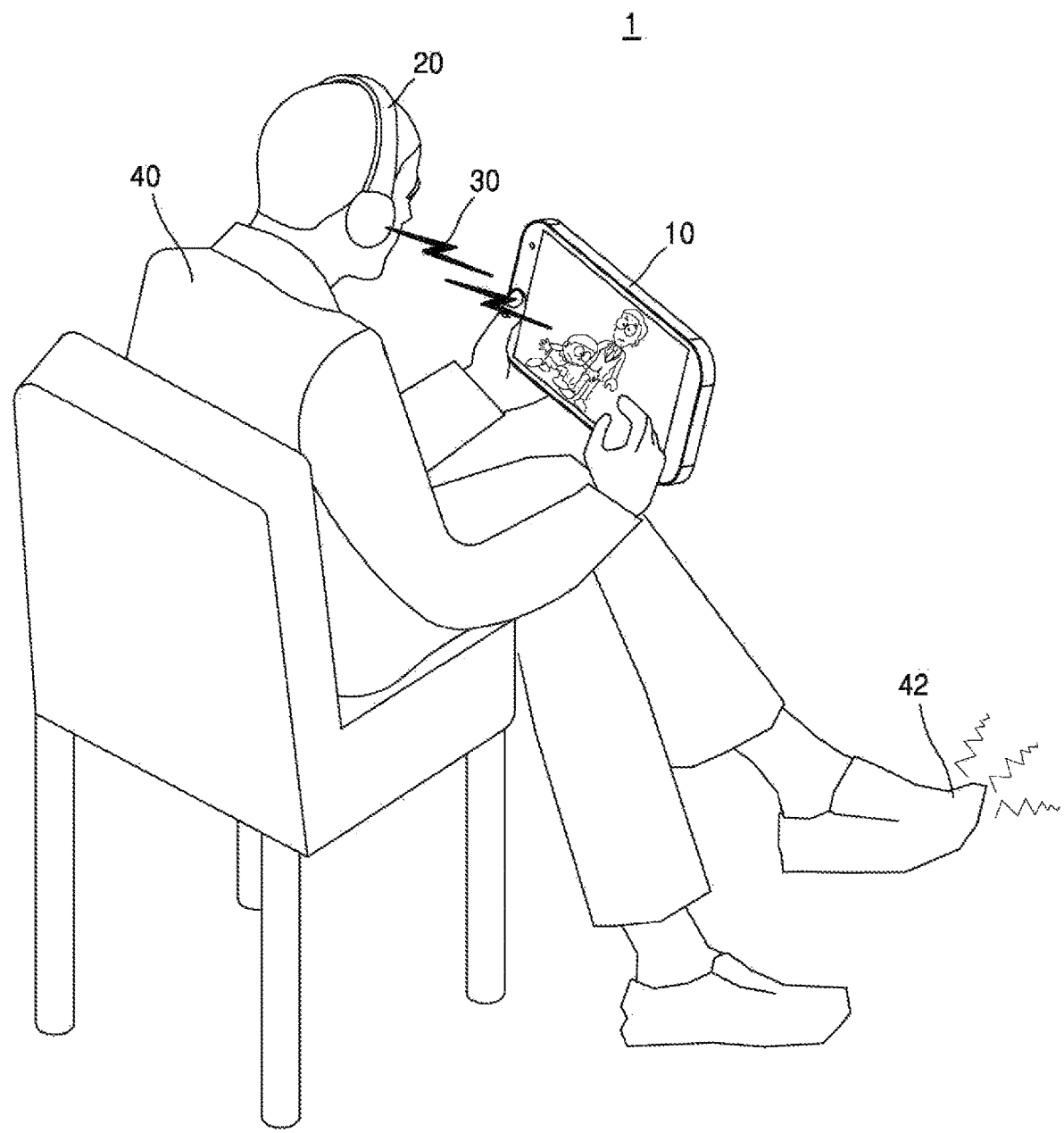
FIG. 1 is a diagram for explaining a system for providing somatic senses corresponding to content, according to an exemplary embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The terms used in this specification are those general terms currently widely used in the art in consideration of functions regarding the present disclosure, but the terms may vary according to the intention of those of ordinary skill in the art, precedents, or new technology in the art. Thus, the terms used in the specification should be understood not as simple names but based on the meaning of the terms and the overall description of the present disclosure.

While such terms as "first", "second", etc., may be used to describe various components, such components must not be limited to the above terms. The above terms are used only to distinguish one component from another.

The terms used in the present specification are merely used to describe particular embodiments, and are not intended to limit the present disclosure. An expression used in the singular encompasses the expression of the plural, unless it has a clearly different meaning in the context. It will be understood that when a region is referred to as being "connected to" another region, it can be directly or indirectly connected to the other region. That is, for example, intervening regions may be present. It will be further understood that the terms "comprises" and/or "comprising" used herein specify the presence of stated features or components, but do not preclude the presence or addition of one or more other features or components.

As used herein, the terms, e.g., "the", etc., are intended to include the plural forms as well, unless the context clearly indicates otherwise. When a certain embodiment may be implemented differently, a specific process order may be performed differently from the described order. For example, two consecutively described processes may be performed substantially at the same time or performed in an order opposite to the described order.

The expressions such as "in some embodiments" or "in an embodiment" do not indicate the same embodiment.

The present disclosure may be described in terms of functional block components and various processing steps. Such functional blocks may be realized by any number of hardware and/or software components configured to perform the specified functions. For example, the functional blocks may be realized by at least one micro-processor or circuits for performing certain functions. Also, the functional blocks may be realized with any programming or scripting language. The functional blocks may be realized in the various algorithms that are executed on one or more processors. Furthermore, the present disclosure could employ any number of conventional techniques for electronics configuration, signal processing and/or control, data processing and the like. The words "mechanism", "element", "means", and "configuration" are used broadly and are not limited to mechanical or physical embodiments.

Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

In the present specification, a wearable device indicates an electronic device that a user may wear. For example, the wearable device may be a watch, glasses, earrings, a necklace, earphones, earring-type accessories, a headband, a helmet, or the like. However, the wearable device is not limited thereto and may be implemented as a device that may be directly attached to or detached from a body part of the user. For example, the wearable device may be of a patch type and may be attached to or detached from a body part of the user in a contact or non-contact manner. Alternatively, the wearable device may be inserted into the body of the user. For example, the wearable device may be implemented as epidermal electronics (or electronic skin (E-skin)), E-tattoo, or the like and thus may be inserted into the epidermis or dermis through a surgical operation.

In the present specification, content may be various pieces of information or items which are provided via Internet or computer communication by processing texts, signs, voices, sounds, images, videos, etc. in a digital manner. For example, the content may include music, movies, games, or the like.

In addition, a somatic sense used herein indicates a sense that is perceived and delivered by information obtained from a skin surface and from within the body, and examples of the somatic sense may be a tactile sense, a pressure sense, a vibration sense, a temperature sense, sensations in internal organs, etc.

Hereinafter, the present disclosure will be described in detail with reference to the attached drawings.

FIG. 1 is a diagram for explaining a system 1 for providing somatic senses 42 corresponding to content, according to an exemplary embodiment.

FIG. 1 illustrates an example of a method by which the system 1 provides a user 40 with the somatic sense 42 corresponding to the content. The system 1 may include an electronic device 10 and an external device 20 that is connected to the electronic device 10 via a network 30.

Referring to FIG. 1, while wearing the external device 20 that may correspond to a wearable device on the head of the user 40, the user 40 uses content that is being played on the electronic device 10.

The expression "using content" may include reading, looking at, listening to, watching, playing content, according to a content type.

The electronic device 10 may provide the user 40 with the somatic sense 42 corresponding to the content. For example, the electronic device 10 may generate somatosensory data by analyzing somatosensory elements included in the content.

The somatosensory elements included in the content may indicate somatic senses that may be empirically expected as being evoked by physical effects, active or passive actions of a subject, an emotional state of the subject, etc. in specific content.

For example, when the content includes a passive action in which a certain subject's foot is stepped on by another subject, it may be empirically expected that the certain subject whose foot is stepped on may feel somatic senses including a pressure sense upon the foot, warm feeling in the foot, etc. Thus, the somatosensory elements included in the content may correspond to the pressure sense upon the foot, the warm feeling in the foot, and the like.

The somatosensory data may be data that includes information regarding types of somatic senses, locations where the somatic senses are evoked, points in time when the somatic senses are evoked, intensities of the somatic senses, frequencies of the somatic senses, etc., corresponding to somatosensory elements included in certain content the data being synchronized with the somatosensory elements included in the certain content. The somatosensory data may be data including the above information corresponding to the somatosensory elements, at a point in time that is synchronized with a point in time when the somatosensory elements of the certain content are evoked.

Based on the obtained somatosensory data, the electronic device 10 may obtain an ultrasound driving signal for arousing the user to the somatic sense 42 that is similar to the somatosensory elements included in the content. The ultrasound driving signal may be a signal by which an ultrasound transducer is controlled to output an ultrasound signal having a certain type, intensity, frequency, etc.

The electronic device 10 may obtain a brain map in which structures and functions of respective regions of the brain are represented. Based on the obtained brain map and somatosensory data, the electronic device 10 may determine a region of the brain that needs to be stimulated to arouse the user 40 to the somatic sense 42 corresponding to the somatosensory data. The electronic device 10 may stimulate the determined region of the brain with an ultrasound signal and thus may obtain the ultrasound driving signal for arousing the user 40 the somatic sense 42 corresponding to the somatosensory data.

Based on the obtained ultrasound driving signal, the electronic device 10 may stimulate a certain region of the brain which is related to a function of a certain body part of the user 40 and thus may arouse the user 40 to the somatic sense 42 corresponding to the somatosensory element of the content without directly simulating the certain body part.

Accordingly, the electronic device 10 may provide the user 40 with various somatic senses 42 without additional devices that need to be placed on body parts of the user 40 in order to deliver physical effects to the user 40.

The electronic device 10 may transmit the obtained ultrasound driving signal to the external device 20 connected to the electronic device 10 via the network 30.

Also, in another exemplary embodiment, the electronic device 10 may be connected to the external device 20 in a wired manner.

The external device 20 may generate an ultrasound signal corresponding to the ultrasound driving signal received from the electronic device 10 and output the ultrasound signal to a certain region of the brain of the user 40, thereby providing the user 40 with the somatic sense 42 corresponding to the somatosensory element included in the content.

Figure 2:
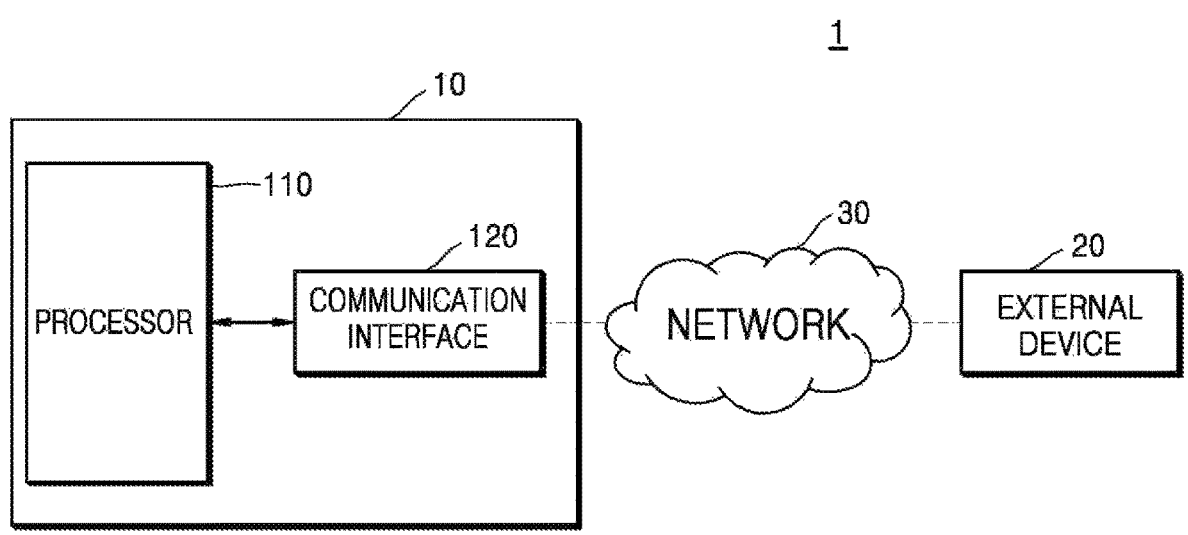
FIG. 2 is a block diagram of the system for providing somatic senses corresponding to the content, according to an exemplary embodiment.

FIG. 2 is a block diagram of the system 1 for providing somatic senses corresponding to content, according to an exemplary embodiment.

The system 1 may include the electronic device 10 and the external device 20 that is connected to the electronic device 10 via the network 30.

The electronic device 10 may include a processor 110 and a communication interface 120.

The processor 110 may include at least one processor. The processor 110 may generally control all operations of the electronic device 10 and process data and signals. In addition, the processor 110 may be operated by at least one software module that is generated by executing program code stored in a memory (not shown).

The processor 110 may stimulate a certain region of the user's brain and thus may obtain an ultrasound signal for evoking somatic senses corresponding to somatosensory data of the content.

In an exemplary embodiment, the content may include somatosensory elements. The somatosensory data may include information corresponding to the somatosensory elements of the content, for example, types of somatic senses, locations where the somatic senses are evoked, points in time when the somatic senses are evoked, intensities of the somatic senses, frequencies of the somatic senses, etc. In addition, the somatosensory data may be synchronized with the somatosensory elements of the content.

For example, the synchronization of the somatosensory data with the somatosensory elements in the content may indicate that the somatosensory data includes information regarding a point in time when each somatosensory element of the content is evoked.

In an exemplary embodiment, the processor 110 may receive the somatosensory data corresponding to certain content from an external server and the external device 20, generate the somatosensory data based on an input received from a user input interface (not shown), generate the somatosensory data by analyzing the somatosensory elements directly included in the content, or obtain the somatosensory data based on a combination of the aforementioned actions.

An ultrasound driving signal may be a signal for controlling generation and output of an ultrasound signal. Accordingly, an ultrasound driving signal for evoking somatic senses corresponding to somatosensory data of content may be a signal for controlling generation of an ultrasound signal for evoking somatic senses corresponding to somatosensory data and output of the generated ultrasound signal.

In an exemplary embodiment, the processor 110 may obtain the ultrasound driving signal based on at least one of content feature information indicating features of the content and user characteristic information indicating characteristics of the user using the content. The content feature information may include at least one of a type of content, brightness of a screen to which the content is output, and volume of output audio of the content. The user characteristic information may include at least one of a threshold value regarding a certain stimulus to the user, a recognition time, preference for a certain somatic sense, and age of the user.

In an exemplary embodiment, the processor 110 may transmit the ultrasound driving signal to the external device 20 and may perform correction on the obtained ultrasound driving signal based on at least one of a delay time taken to output ultrasound waves to the external device 20, a delay time taken for sound pressure of the output ultrasound waves to stimulate the user's brain, and a delay time taken for the user to actually recognize somatic senses evoked by the stimuli to the brain.

In an exemplary embodiment, the processor 110 may perform correction on the obtained ultrasound driving signal based on characteristic information regarding the external device 20, for example, an oscillation frequency of the external device 20 that generates and outputs the ultrasound signal, a variation in outputs of ultrasound signals according to voltages or waveforms thereof, etc.

In addition, the processor 110 may receive the characteristic information regarding the external device 20 from the external device 20 in real time. Based on the characteristic information regarding the external device 20 that is received in real time, the processor 110 may perform the correction on the ultrasound driving signal. For example, the external device 20 may have varying physical features, e.g., performance degradation due to fatigue accumulated while the external device 20 is used. The processor 110 may receive the characteristic information regarding the external device 20 from the external device 20 in real time and may generate an ultrasound driving signal that may optimally arouse the user to somatic senses by performing the correction on the ultrasound driving signal.

In an exemplary embodiment, the processor 110 may perform individualized correction on the generated ultrasound driving signal based on the user characteristic information. For example, each user may have a different threshold value for recognizing an ultrasound signal, which is output to a certain region of the brain, as a stimulus. Accordingly, the processor 110 may perform the individualized correction via which cognitive characteristics of the user may be reflected to the obtained ultrasound driving signal, thereby generating an ultrasound driving signal for evoking the somatic senses which is optimized for each user.

The communication interface 120 may transmit, to the external device 20, the ultrasound driving signal generated by the processor 110.

In an exemplary embodiment, the communication interface 120 may transmit the ultrasound driving signal to the external device 20 connected thereto in a wired or wireless manner. The communication interface 120 may transmit in real time the ultrasound driving signal to the external device 20 connected to the communication interface 120 via the network 30.

In an exemplary embodiment, the communication interface 120 may transmit the ultrasound driving signal to the external device 20 that is determined by the processor 110 as a device for generating and outputting an ultrasound signal. The external device 20 may include an ultrasound transducer.

Figure 3:
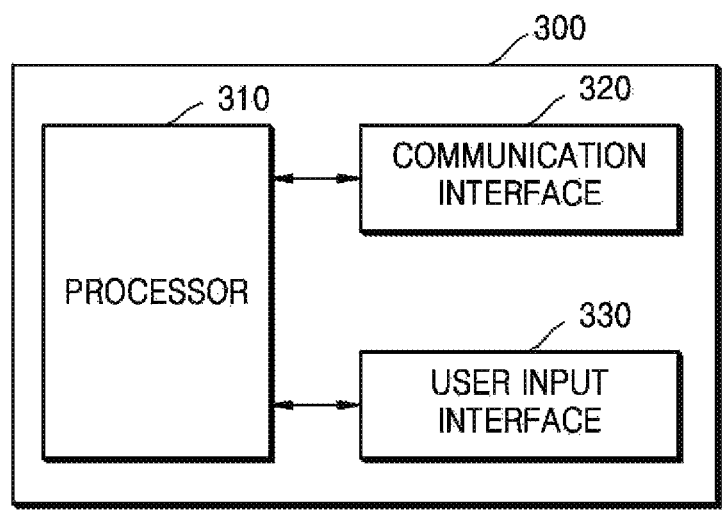
FIG. 3 is a block diagram of an electronic device for providing somatic senses corresponding to content, according to an exemplary embodiment.

FIG. 3 is a block diagram of an electronic device 300 for providing somatic senses corresponding to content, according to an exemplary embodiment.

The electronic device 300 may correspond to the electronic device 10 of FIGS. 1 and 2. Thus, a processor 310 of FIG. 3 may correspond to the processor 110 of FIG. 2, and a communication interface 320 may correspond to the communication interface 120 of FIG. 2. Therefore, the descriptions provided with reference to FIGS. 1 and 2 will not be repeated.

The electronic device 300 may further include a user input interface 330 in addition to the processor 310 and the communication interface 320.

The user input interface 330 may receive various instructions from the user. The user input interface 330 may include at least one of a key, a touch panel, and a pen recognition panel.

In an exemplary embodiment, the user input interface 330 may receive a user input via a graphical user interface (GUI) that is displayed on a display (not shown).

In an exemplary embodiment, the user input interface 330 may receive a user input for generating somatosensory data corresponding to somatosensory elements included in content.

In an exemplary embodiment, the user input interface 330 may receive user characteristic information indicating user characteristics that include at least one of a threshold value regarding a certain stimulus to the user, a recognition time, preference for a certain somatic sense, and age of the user.

Also, in an exemplary embodiment, the user input interface 330 may receive an input regarding content feature information indicating features of the content that include at least one of a content type, brightness of a screen to which the content is output, volume of output audio of the content.

Figure 4:
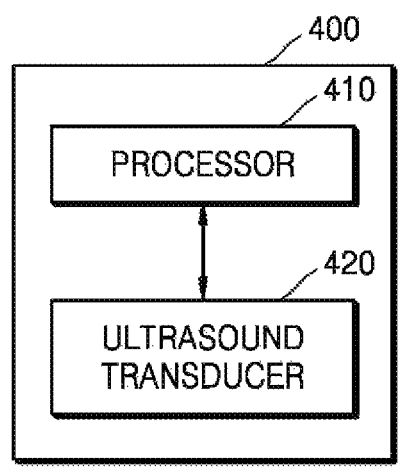
FIG. 4 is a block diagram of a wearable device for providing somatic senses corresponding to content, according to an exemplary embodiment.

FIG. 4 is a block diagram of a wearable device 400 for providing somatic senses corresponding to content, according to an exemplary embodiment.

The wearable device 400 denotes an electronic device that the user may wear. Also, the wearable device 400 may be directly attached to or detached from the user's body or may be inserted therein.

The wearable device 400 may output an ultrasound signal to a certain region of the user's brain and may be placed on the user's head as a device for providing a content-based somatic sense. However, the wearable device 400 is not limited thereto. The wearable device 400 may be placed on body parts of the user other than the head and may be embodied as a type including separate accessories that may be placed on the user's head.

The wearable device 400 may include a processor 410 and an ultrasound transducer 420. However, the structure of the wearable device 400 is not limited thereto, and the wearable device 400 may be embodied by more or less components than the components shown in FIG. 4.

The processor 410 may include at least one processor (not shown). The processor 410 may generally control all operations of the wearable device 400 and may process data and signals. Also, the processor 410 may be operated by at least one software module generated by executing program code that is stored in a memory (not shown).

The processor 410 may obtain an ultrasound driving signal for evoking somatic senses corresponding to somatosensory data of the content by simulating a certain region of the user's brain.

In an exemplary embodiment, the content may include somatosensory elements, and the somatosensory data corresponding to the content may include information corresponding to the somatosensory elements of the content, for example, types of the somatic senses, locations where the somatic senses are evoked, points in time when the somatic senses are evoked, intensities of the somatic senses, frequencies of the somatic senses, and the like. In addition, the somatosensory data may be synchronized with the somatosensory elements of the content.

In an exemplary embodiment, the processor 410 may receive the somatosensory data corresponding to certain content from an external server (not shown) and an external device (not shown), may generate the somatosensory data based on an input from a user input interface (not shown), may generate the somatosensory data by analyzing the somatosensory elements that are directly included in the content, and may acquire the somatosensory data based on a combination of the aforementioned actions.

In an exemplary embodiment, the processor 410 may receive the ultrasound driving signal for evoking the somatic senses corresponding to the somatosensory data, from the external server and the external device.

In another exemplary embodiment, the processor 410 may generate the ultrasound driving signal for evoking the somatic senses corresponding to the somatosensory data, based on the obtained somatosensory data. The processor 410 may receive, from the external server or the external device, information regarding types of the somatic senses that may be felt on a human skin surface or under the skin, locations where the somatic senses are evoked, and regions of the brain with regard to the locations. The processor 410 may generate the ultrasound driving signal for evoking the somatic senses corresponding to the somatosensory data, based on the received information.

The ultrasound driving signal may be a signal for controlling generation and output of an ultrasound signal. For example, based on the received information regarding the regions of the brain, the ultrasound driving signal may include control signals regarding locations of transducers, which are included in the ultrasound transducer 420 and need to be operated to allow the ultrasound transducer 420 on the user's head to evoke a certain somatic sense, the number of transducers, oscillation frequencies of ultrasound signals output from the transducers, output intensities of the ultrasound signals, an output repetition period of the ultrasound signals, an amplitude change of the ultrasound signals, or the like.

In an exemplary embodiment, the processor 410 may perform correction on the obtained ultrasound driving signal based on at least one of a delay time taken for the ultrasound transducer 420 to transmit the ultrasound driving signal to output ultrasound waves, a delay time taken for sound pressure of the output ultrasound waves to stimulate the user's brain, and a delay time taken for the user to actually recognize somatic senses evoked by the stimuli to the brain.

In an exemplary embodiment, the processor 410 may perform the correction on the obtained ultrasound driving signal based on feature information regarding features of the ultrasound transducer 420, e.g., an oscillation frequency of the ultrasound transducer 420 that outputs ultrasound signals, a variation in outputs of the ultrasound signals according to a voltage or a wave form, etc.

In addition, the processor 410 may generate feature information indicating physical features of the ultrasound transducer 420 in real time. The processor 410 may perform the correction on the obtained ultrasound driving signal based on the generated feature information of the ultrasound transducer 420. For example, the ultrasound transducer 420 may have varying physical features, e.g., performance degradation due to fatigue accumulated while the ultrasound transducer 420 is used. The processor 410 may generate the feature information regarding the ultrasound transducer 420 in real time and may perform the correction on the ultrasound driving signal based on the generated feature information, thereby generating an ultrasound driving signal for evoking the somatic senses which is optimized for the user.

In an exemplary embodiment, the processor 410 may perform individualized correction on the obtained ultrasound driving signal based on the user characteristics information. For example, each user may have a different threshold value for recognizing an ultrasound signal, which is output to a certain region of the brain, as a stimulus. Accordingly, the processor 410 may perform the individualized correction via which cognitive characteristics of the user may be reflected to the obtained ultrasound driving signal, thereby generating an ultrasound driving signal for evoking the somatic senses which is optimized for each user.

In an exemplary embodiment, the processor 410 may determine an initial mounting location of the wearable device 400 and may determine, based on the determined initial mounting location, whether a variation in a mounting location of the wearable device 400 is greater than a certain threshold value.

For example, the processor 410 may control the ultrasound signal for evoking certain somatic senses to be output to the user's brain and may receive feedback regarding whether the user has detected the certain somatic senses, thereby determining the initial mounting location of the wearable device 400.

Also, in another exemplary embodiment, the processor 410 may control the ultrasound signal for evoking the certain somatic senses to be output to the user's brain and may determine how much nerves in the user's brain are activated, thereby determining the initial mounting location of the wearable device 400.

The term 'initial mounting location' of the wearable device 400 may indicate a location of the user's head on which the wearable device 400 is placed in such a manner that an ultrasound signal for evoking a certain somatic sense is to be accurately output to a relevant region of the user's brain.

The processor 410 may accurately place a focus on a relevant region of the user's brain and transmit the ultrasound signal for evoking the certain somatic sense to the relevant region through a process of determining the initial mounting location of the wearable device 400. Detailed descriptions in this regard will be provided later with reference to FIG. 13.

In an exemplary embodiment, the processor 410 may use a capacitive sensor (not shown) to determine an output value of the capacitive sensor in an initial mounting state of the wearable device 400. The processor 410 may keep monitoring the output value of the capacitive sensor while the user wears the wearable device 400 and uses content such that the processor 410 may determine whether a variation in the output value of the capacitive sensor is greater than a certain threshold value.

When the variation in the output value of the capacitive sensor is greater than the certain threshold value, the processor 410 may stop the ultrasound transducer 420 from outputting the ultrasound signals. In addition, the processor 410 may output at least one of a visual alarm and a sound alarm for guiding the wearable device 400 to a mounting location thereof in such a manner that the mounting location corresponds to the initial mounting location of the wearable device 400.

The processor 410 may keep monitoring the mounting location of the wearable device 400, and when the wearable device 400 is out of the initial mounting location thereof to an extent greater than a certain threshold value, the processor 410 guides the wearable device 400 to a re-mounting location. Thus, the processor 410 may accurately place a focus on a relevant region of the user's brain and transmit the ultrasound signal for evoking the certain somatic sense to the relevant region. Moreover, when the mounting location of the wearable device 400 is out of the initial mounting location thereof to an extent greater than the certain threshold value, the processor 410 may stop outputting the ultrasound signals and thus may prevent in advance accidents, which may occur when the ultrasound signals are output to other regions instead of target areas.

The ultrasound transducer 420 outputs the ultrasound signals to the user's brain based on the ultrasound driving signals.

The ultrasound transducer 420 may include transducers. The transducers may output ultrasound signals to certain regions of the user's brain according to the ultrasound driving signals. The ultrasound transducer 420 may include transducers each including either a single device or multiple devices, or transducers including a combination thereof.

Figure 5:
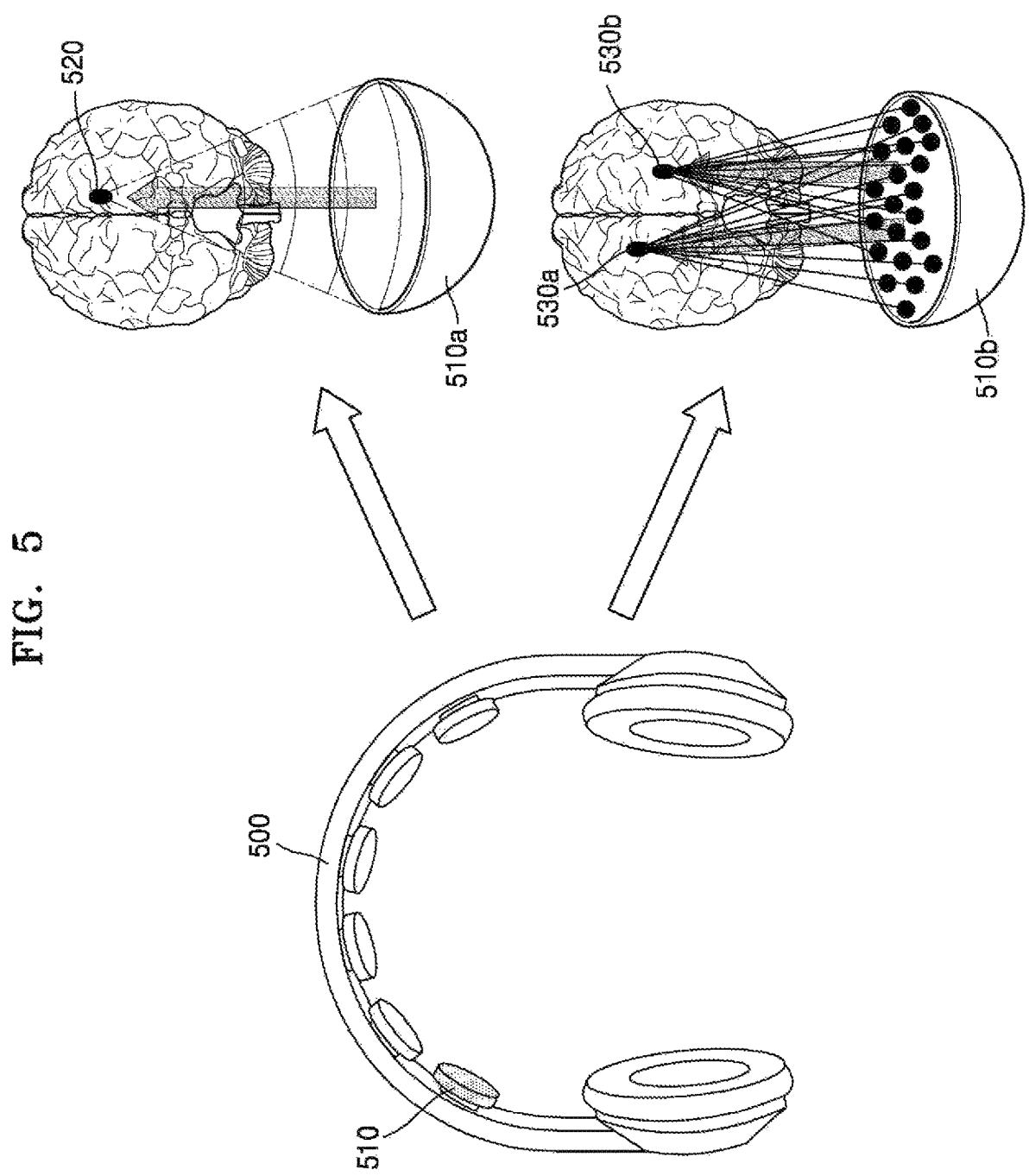
FIG. 5 is a diagram for explaining a method of outputting an ultrasound signal by an ultrasound transducer included in a wearable device, according to an exemplary embodiment.

FIG. 5 is a diagram for explaining a method of outputting ultrasound signals by an ultrasound transducer 510 included in a wearable device 500, according to an exemplary embodiment.

The wearable device 500 may correspond to the wearable device 400 of FIG. 4.

Referring to FIG. 5, the wearable device 500 may include ultrasound transducers 510 and may be placed on the user's head.

The ultrasound transducer 510 may output the ultrasound signals based on ultrasound driving signals. The ultrasound transducer 510 may convert an electrical signal into an ultrasound signal based on information included in the ultrasound driving signals and thus may generate the ultrasound signals for evoking somatic senses corresponding to somatosensory elements of content.

In an exemplary embodiment, the ultrasound transducer 510 may be embodied as a transducer 510a including a single device or as a transducer 510b including multiple devices. Alternatively, the ultrasound transducer 510 may be embodied as a combination of the transducer 510a and the transducer 510b.

The ultrasound transducer 510 may adjust a delay time when the ultrasound signals are output and thus may focus ultrasound signals on a certain region. Also, the ultrasound transducer 510 may include a mechanical structure used to focus the ultrasound signals on the certain region.

The transducer 510a including the single device may output the ultrasound signals that are simultaneously focused only on one region 520, but the transducer 510b including the devices may output the ultrasound signals that are simultaneously focused on one region or regions 530a and 530b.

The ultrasound transducer 510 may output the ultrasound signals that are focused on a certain region of the user's brain that is related to a function of a certain body part of the user, based on the ultrasound driving signals, and may provide the user with the somatic senses corresponding to the somatosensory elements of the content.

Figure 6:
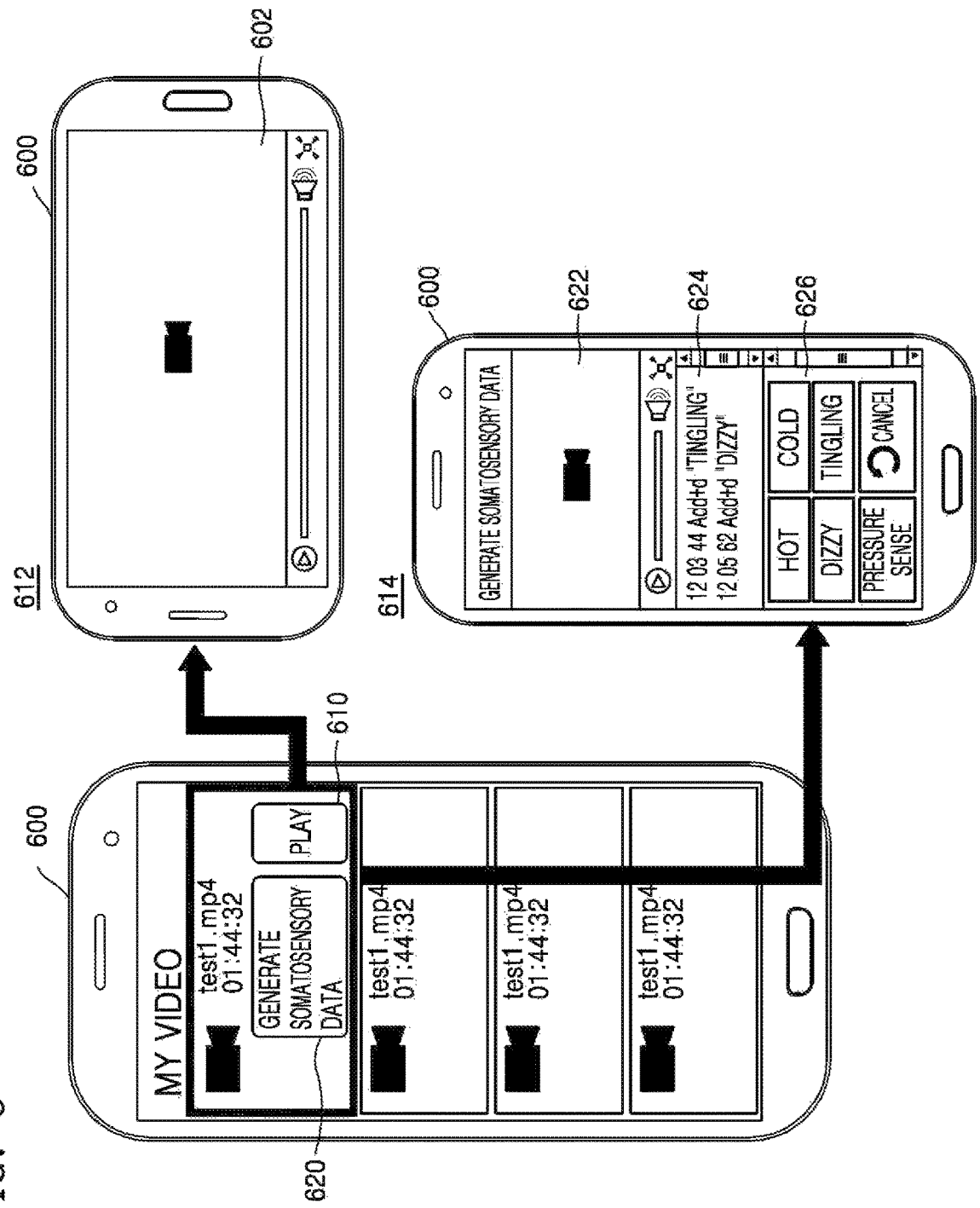
FIG. 6 is a diagram for explaining a method of providing somatic senses corresponding to content, according to an exemplary embodiment.

FIG. 6 is a diagram for explaining a method of providing somatic senses corresponding to content, according to an exemplary embodiment.

FIG. 6 illustrates an exemplary embodiment in which an electronic device 600 provides the somatic senses corresponding to the content. The electronic device 600 may correspond to at least one of the electronic device 300 of FIG. 3 and the wearable device 400 of FIG. 4.

The electronic device 600 may provide a somatosensory data generation mode 614, in which somatosensory data corresponding to somatosensory elements of the content may be generated based on a user input, and a somatic sense playing mode 612 in which content-based somatic senses are provided to the user based on the generated somatosensory data.

The electronic device 600 may include a display and may provide, through the display, a user interface for selecting the somatosensory data generation mode 614 and the somatic sense playing mode 612 with regard to the certain content, wherein in the somatic sense playing mode 612, the somatosensory data is played.

For example, when the electronic device 600 receives a user input for selecting a button 610, the electronic device 600 may provide the somatic sense playing mode 612 with regard to content test1.mp4. The electronic device 600 may play the content test1.mp4 on a region 602 of the display and at the same time, may provide the user with somatic senses based on the somatosensory data that is synchronized with the content test1.mp4.

As another example, when the electronic device 600 receives a user input for selecting a button 620, the electronic device 600 may provide the somatosensory data generation mode 614 with regard to the content test1.mp4. The electronic device 600 may play the content test1.mp4 on a region 622 of the display and may provide an editing window 624, on which the user may directly input the somatosensory data, on another region of the display based on the content test1.mp4 that is being played. Based on items of the content test1.mp4 that is being played, the user may input, to the editing window 624, the somatic senses corresponding to the somatosensory elements included in the content test1.mp4.

The electronic device 600 may provide somatic sense generation buttons 626 corresponding to types of somatic senses on a region of the display. When the electronic device 600 receives a user input for selecting any one of the somatic sense generation buttons 626, the electronic device 600 may generate the somatosensory data based on the types of the somatic senses corresponding to a point in time when the button is selected and to the selected button. For example, in the somatosensory data generation mode 614 with regard to the content test1.mp4, when the user provides an input of selecting a 'tingling' button included in the somatic sense generation buttons 626 at a point in time 12:03:44 when the content test1.mp4 is played, the electronic device 600 may generate the somatosensory data including a 'tingling' somatic sense and synchronized with the point in time 12:03:44 when the content test1.mp4 is played.

Figure 7:
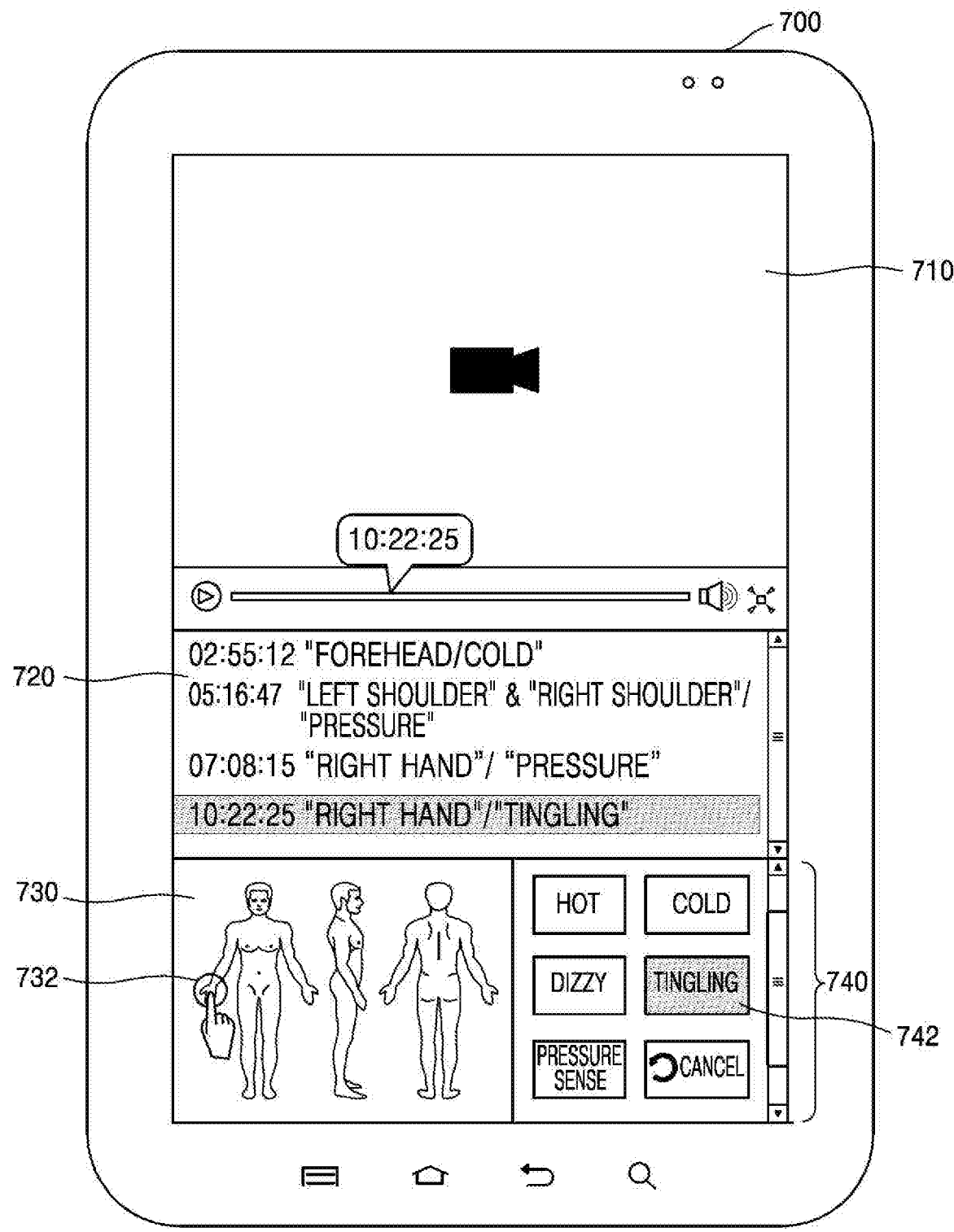
FIG. 7 is a diagram for explaining a method of generating somatosensory data corresponding to content, according to an exemplary embodiment.

FIG. 7 is a diagram for explaining a method of generating somatosensory data corresponding to content, according to an exemplary embodiment.

FIG. 7 illustrates the method of generating, by an electronic device 700, the somatosensory data based on a user input. The electronic device 700 may correspond to at least one of the electronic device 300 of FIG. 3, the wearable device 400 of FIG. 4, and the electronic device 600 of FIG. 6.

The electronic device 700 may include a display and may provide, through the display, a user interface for receiving an input for generating somatosensory data corresponding to certain content. The electronic device 700 may play the content on a region 710 of the display. Also, the electronic device 700 may provide an editing window 720, on which the user may directly provide the input for generating the somatosensory data, on another region of the display, based on the content being played. Based on the content being played, the user may input, to the editing window 720, somatic senses corresponding to somatosensory elements of the content.

The electronic device 700 may have a model image 730 showing human bodies and somatic sense generation buttons 740 respectively corresponding to the somatic senses, on a region of the display. When the electronic device 700 receives a user input for selecting a body part from among the human bodies shown in the model image 730 and a user input for selecting any one of the somatic sense generation buttons 740, the electronic device 700 may generate the somatosensory data based on a point in time when the user inputs are received and the user inputs.

For example, when a user input of selecting the 'right hand' on the model image 730 and a user input of selecting a 'tingling' button 742 from among the somatic sense generation buttons 740 are received at a point in time 10:22:25 when certain content is played, the electronic device 700 may generate somatosensory data that is synchronized with the point in time 10:22:25 and includes a 'tingling' somatic sense on the 'right hand'.

FIG. 7 only illustrates the model image 730 showing the human bodies and the somatic sense generation buttons 740 as an example of a user interface for generating the somatosensory data corresponding to the certain content. However, the electronic device 700 may provide various types and forms of user interfaces for inputting various pieces of information that may be included in the somatosensory data.

Figure 8A:
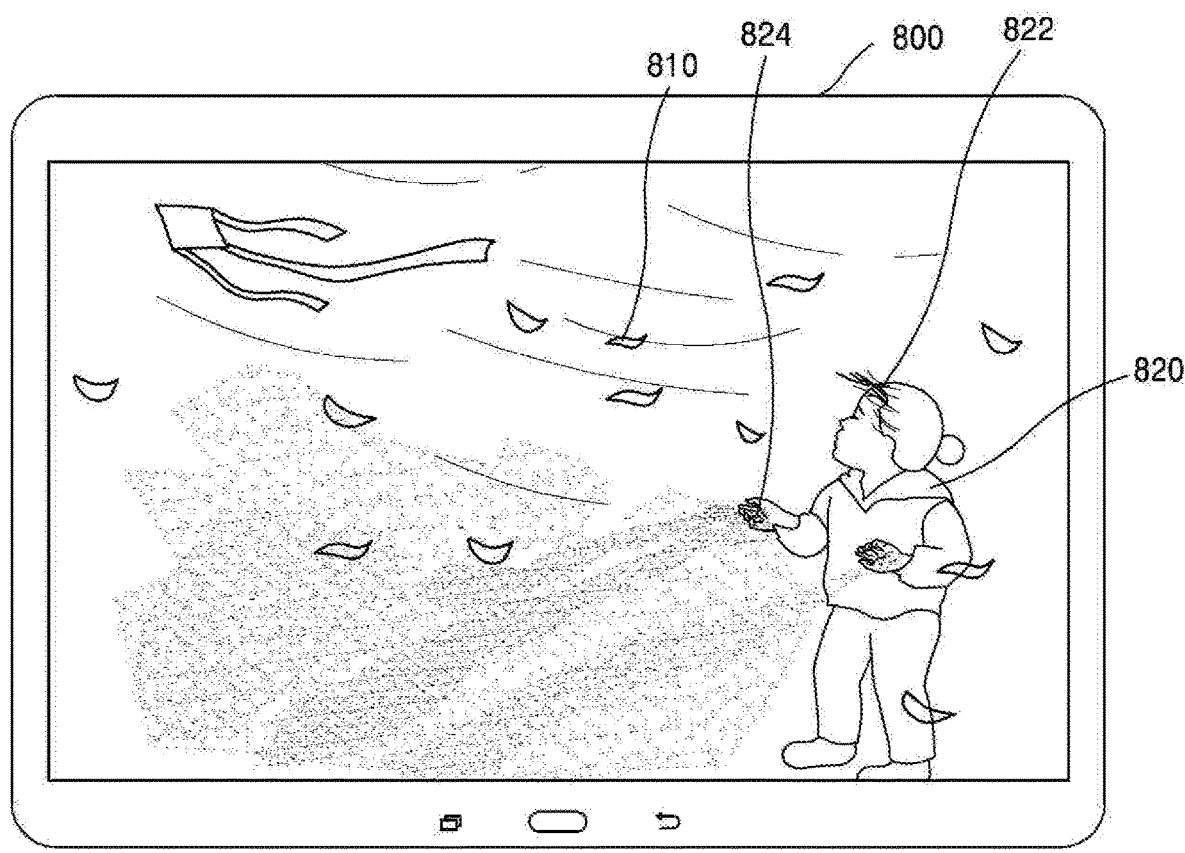
FIGS. 8A and 8B are diagrams for explaining a method of generating somatosensory data corresponding to content, according to another exemplary embodiment.
Figure 8B:
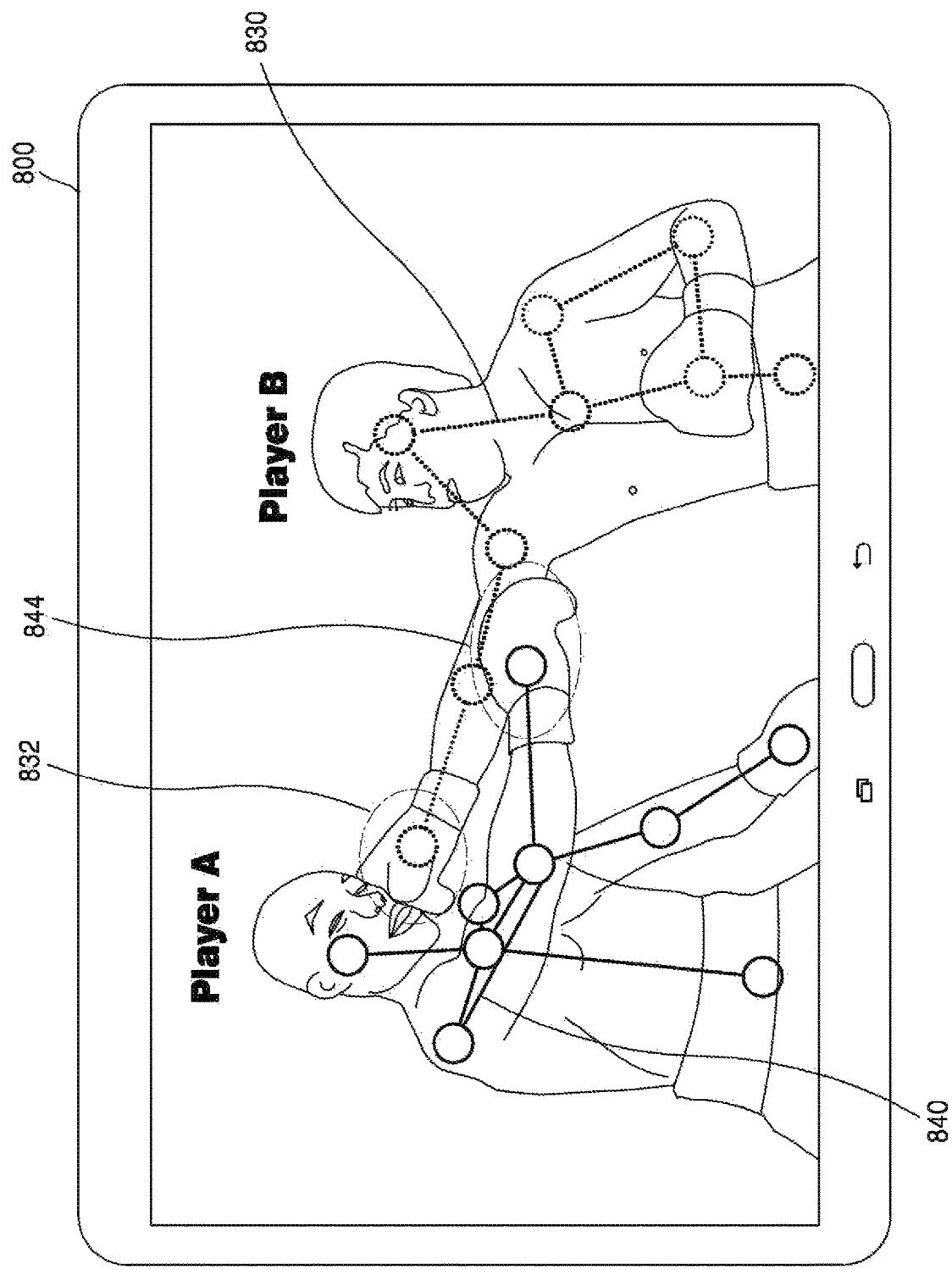

FIGS. 8A and 8B are diagrams for explaining a method of generating somatosensory data corresponding to content, according to another exemplary embodiment.

FIGS. 8A and 8B illustrate the method of generating, by an electronic device 800, the somatosensory data corresponding to content by analyzing somatosensory elements included in the content. The electronic device 800 may correspond to at least one of the electronic device 300 of FIG. 3, the wearable device 400 of FIG. 4, and the electronic device 600 of FIG. 6.

FIG. 8A illustrates a method of analyzing, by the electronic device 800, the somatosensory elements that may be empirically expected to be evoked due to physical effects of the content and active or passive actions of a subject.

The electronic device 800 may recognize a direction 810 in which wind blows as a somatosensory element, the direction 810 being included in video content. In the case of content including sounds, the electronic device 800 may recognize a wind blowing sound as a somatosensory element. For example, the electronic device 800 may empirically determine that a somatic sense such as a 'cool sensation' is evoked based on at least one of the direction 810 and the wind blowing sound. The empirical determination may indicate that the electronic device 800 makes a determination based on an existing database or a previous determination.

Moreover, the electronic device 800 may recognize, as somatosensory elements, a shape 822 in which hair of a subject 820 is blowing, and a shape 824 in which sand slips through the fingers of the subject 820, wherein the shapes 822 and 824 are included in video content. In addition, in the case of sound content, the electronic device 800 may recognize, as a somatosensory element, a voice of the subject 820 that is related to a somatosensory expression and included in the content. For example, based on at least one of the shape 822 in which the hair of the subject 820 is blowing, the shape 824 in which the sand slips through the fingers of the subject 820, and the voice of the subject 820 that is related to the somatosensory expression, the electronic device 800 may empirically determine that somatic senses such as a 'tickling sensation' or a 'cool sensation' are evoked.

FIG. 8B illustrates an example in which the electronic device 800 analyzes actions of subjects (i.e., Player A and Player B) included in content and thus analyzes somatosensory elements included in the content.

The electronic device 800 may determine joint models 830 and 840 respectively corresponding to joints of the subjects (i.e., the Player A and the Player B) included in the content. The electronic device 800 may recognize, as a somatosensory element, at least one of directions in which the determined joint models 830 and 840 move, angles of the joint models 830 and 840, and the speed thereof and may determine actions of the subjects (i.e., the Player A and the Player B) and somatic senses that may be empirically expected to be evoked by the actions.

For example, when a region corresponding to the right hand of the joint model 830 of the Player B moves fast towards a region 832 corresponding to the face of the joint model 840 of the Player A, the electronic device 800 may determine that the face of the Player A is hit by the right hand of the Player B. Therefore, the electronic device 800 may empirically determine that somatic senses such as a 'tingling sensation' or a 'pressure sensation' may be respectively aroused in the right hand of the Player B and the face of the Player A.

In addition, when a region corresponding to the right hand of the joint model 840 of the Player A moves fast towards a region 844 corresponding to the right shoulder of the Player B, the electronic device 800 may determine that the right shoulder of the Player B is hit by the right hand of the Player A. Therefore, the electronic device 800 may empirically determine that somatic senses such as a 'tingling sensation' or a 'pressure sensation' may be respectively aroused in the right shoulder of the Player B and the right hand of the Player A.

As illustrated in FIGS. 8A and 8B, the electronic device 800 may analyze items of the content and thus may obtain somatic senses that may be evoked by passive or active actions of the subjects included in the content as well as environmental and physical effects produced by wind, water, fire, snow, ice, etc. around the subjects. A variety of well-known image analysis methods or data analysis methods may be used to analyze items of content. The electronic device 800 may generate the somatosensory data corresponding to the content based on the somatosensory elements that are obtained by analyzing the content.

When the content includes multiple subjects, the electronic device 800 may classify somatic senses that may be aroused in respective subjects and generate pieces of somatosensory data including the classified somatic senses for respective users or may generate somatosensory data including all somatic senses that may be aroused in the subjects. For example, when the electronic device 800 classifies and generates the somatosensory data for each subject, the electronic device 800 may provide the user with the somatic senses that may be aroused in a subject determined according to a user input.

Figure 9:
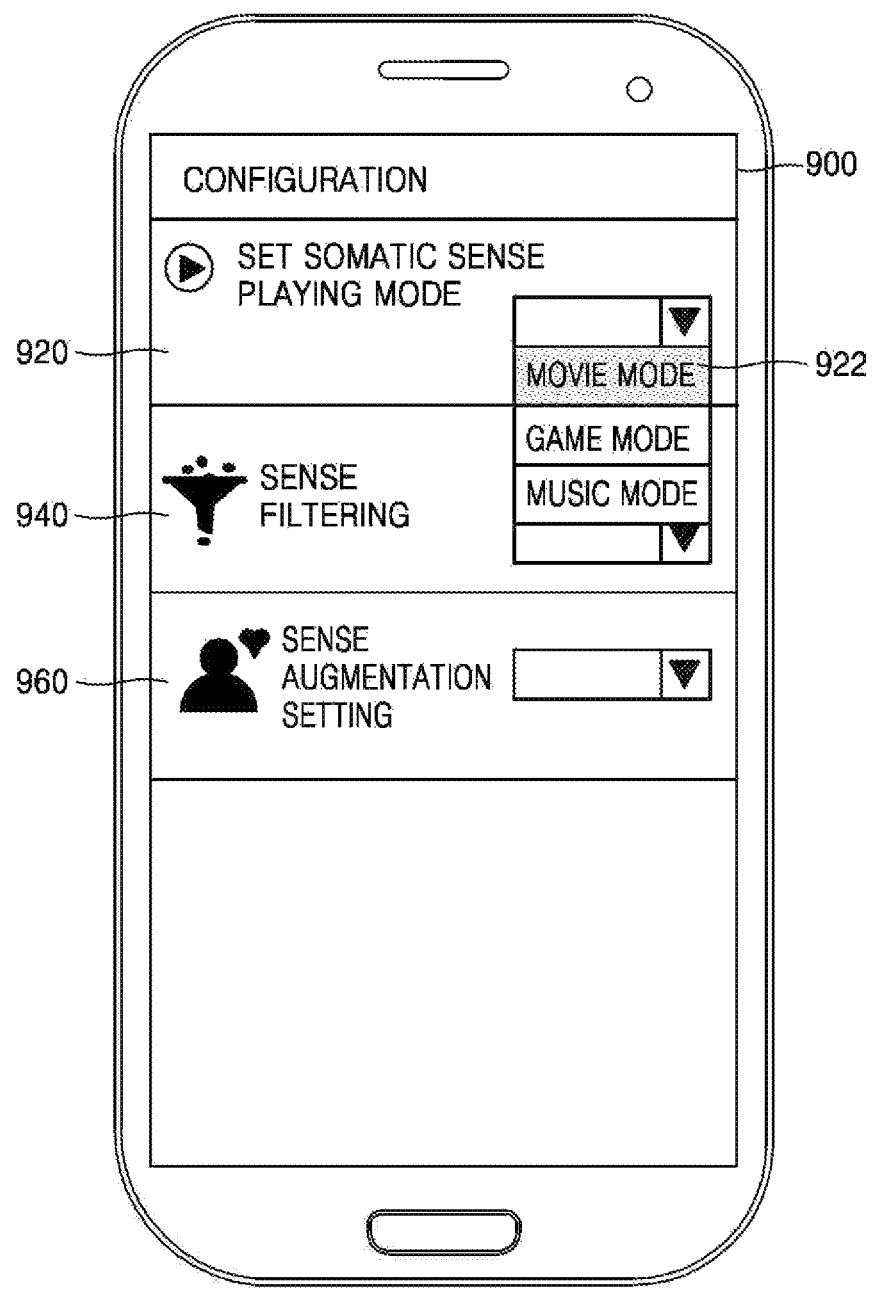
FIG. 9 is a diagram of a user interface according to an exemplary embodiment.

FIG. 9 is a diagram of a user interface according to an exemplary embodiment.

Referring to FIG. 9, the electronic device 300 (refer to FIG. 3) may provide a user interface used to receive a user input for determining a method of providing, by the electronic device 300, somatic senses according to personal preference.

FIG. 9 illustrates that a configuration window 900 is provided by the electronic device 300. However, the present disclosure is not limited thereto. The configuration window 900 may be provided by the electronic device 10 of FIG. 2 or the wearable device 400 of FIG. 4.

For example, the electronic device 300 may provide the user with the configuration window 900 used to select the method of providing the somatic senses. The configuration window 900 may include items regarding a somatic sense playing mode setting 920, sense filtering 940, and sense augmentation setting 960.

Based on the item regarding the somatic sense playing mode setting 920, the electronic device 300 may receive a user input of selecting a mode in which an ultrasound signal corresponding to somatosensory data is output. The item regarding the somatic sense playing mode setting 920 may include sub-items 922 including a movie mode, a game mode, and a music mode. Based on a user input in the somatic sense playing mode setting 920, the electronic device 300 may determine a mode in which an ultrasound signal for arousing the user to the somatic sense is output. Detailed descriptions in this regard will be provided below with reference to FIG. 10.

Based on the item regarding the sense filtering 940, the electronic device 300 may receive a user input regarding a somatic sense that the user wants to remove from the somatic senses included in the somatosensory data. For example, when the user inputs a somatic sense such as a 'stinging sensation' to the item regarding the sense filtering 940, the electronic device 300 may generate ultrasound driving signals for outputting ultrasound signals for evoking other somatic senses except the 'stinging sensation' even though the somatosensory data corresponding to the certain data includes the 'stinging sensation'.

Based on the item regarding the sense augmentation setting 960, the electronic device 300 may receive a user input regarding a somatic sense that the user wants to strengthen among the somatic senses included in the somatosensory data. Based on the user input that is received based on the item regarding the sense augmentation setting 960, the electronic device 300 may generate an ultrasound driving signal for outputting an ultrasound signal for evoking a somatic sense that is selected from among the somatic senses of the somatosensory data and then is augmented.

Figure 10:
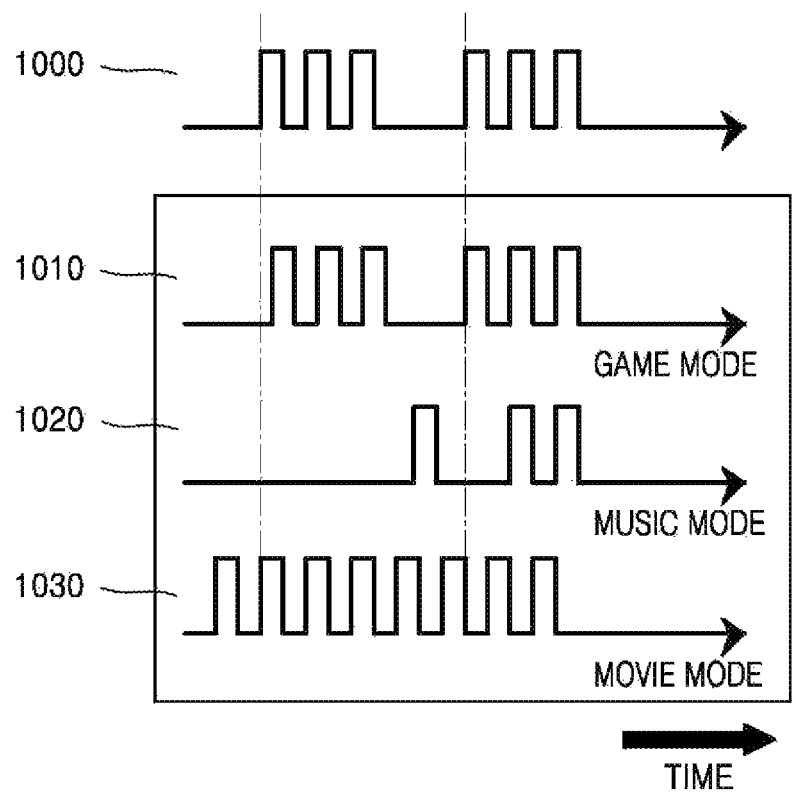
FIG. 10 is a diagram for explaining a method of providing somatic senses according to a somatic sense playing mode, according to an exemplary embodiment.

FIG. 10 is a diagram for explaining a method of providing somatic senses according to a somatic sense playing mode, according to an exemplary embodiment. For example, the somatic sense playing mode may include a game mode, a music mode, and a movie mode.

The electronic device 300 may determine frequencies, intensities, etc. of ultrasound signals that are output to evoke somatic senses, according to the determined somatic sense playing mode.

Referring to FIG. 10, 1000 indicates a timing when somatosensory elements included in content occur according to a play time of the content, and 1010 to 1030 respectively indicate points in time when ultrasound signals corresponding to the somatosensory data synchronized with the content are output according to time when the somatic sense playing mode is set as a game mode, a music mode, and a movie mode.

According to the determined somatic sense playing mode, the electronic device 300 may differently output the ultrasound signals corresponding to the somatosensory elements of the content by adding or removing some somatic senses.

For example, when the somatic sense playing mode is a game mode, the electronic device 300 may generate an ultrasound driving signal for controlling an output of an ultrasound signal for evoking somatic senses corresponding to the user at the same timing as the timing when the somatosensory elements included in the content occur.

As another example, when the somatic sense playing mode is a music mode, the electronic device 300 may remove some somatic senses and generate an ultrasound driving signal for controlling an output of an ultrasound signal for evoking somatic senses a smaller number of times than the ultrasound signal at the timing when the somatosensory elements included in the content occur.

As another example, when the somatic sense playing mode is a movie mode, the electronic device 300 may add some somatic senses and generate an ultrasound driving signal for controlling an output of an ultrasound signal for evoking somatic senses a greater number of times than the ultrasound signal at the timing when the somatosensory elements included in the content occur.

Also, in an exemplary embodiment, the electronic device 300 may generate an ultrasound driving signal that is corrected in real time in consideration of the somatic sense playing mode, a relationship between the somatic sense playing mode and a type of a somatic sense that is most recently provided.

FIG. 10 illustrates that the method of providing the somatic senses according to the somatic sense playing mode is implemented by the electronic device 300. However, the present disclosure is not limited thereto. The method may be implemented by the electronic device 10 of FIG. 2 or the wearable device 400 of FIG. 4.

Figure 11:
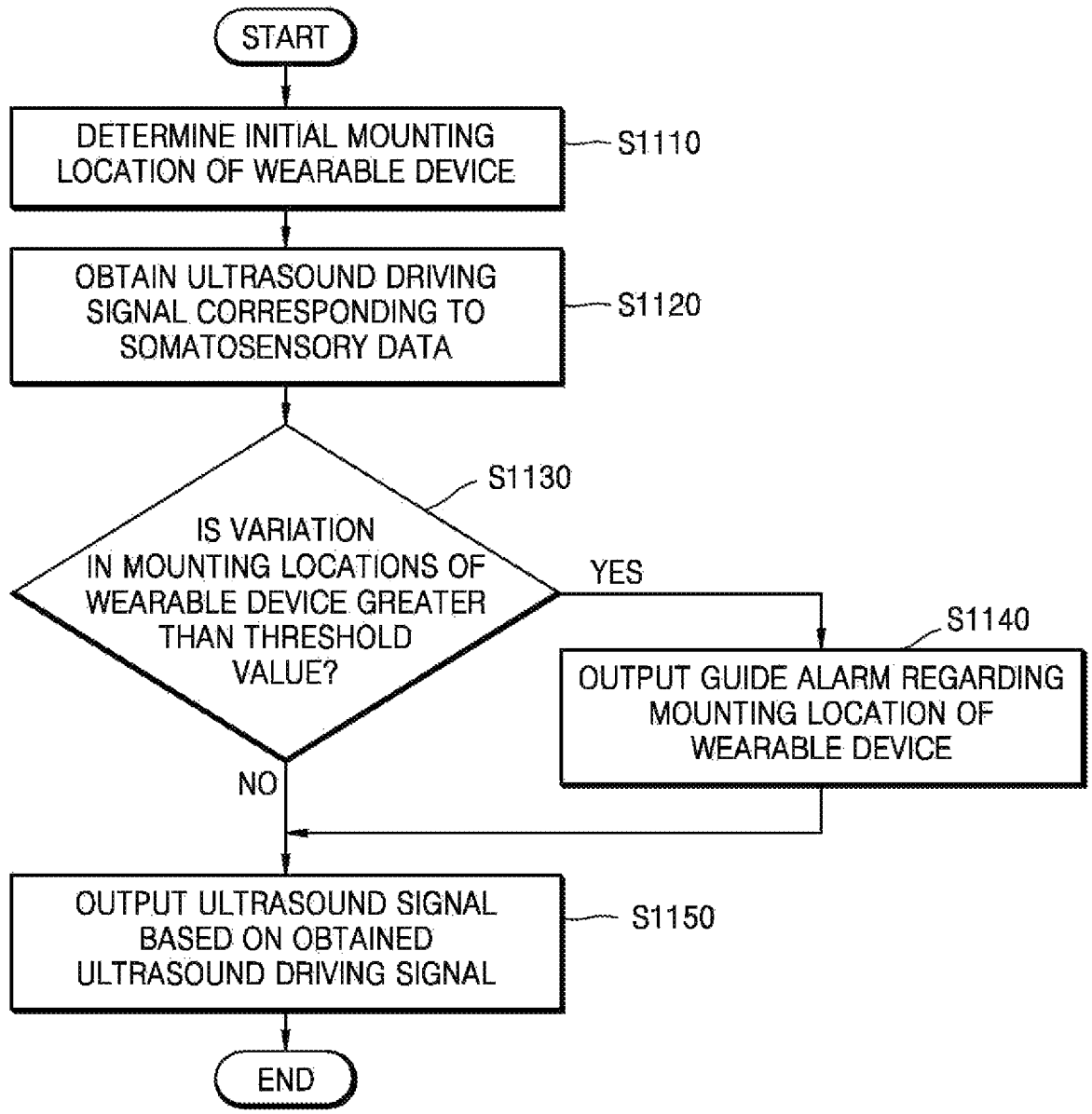
FIG. 11 is a flowchart of a method of providing, by the wearable device, somatic senses corresponding to content, according to an exemplary embodiment.

FIG. 11 is a flowchart of a method of providing, by the wearable device 400, somatic senses corresponding to content, according to an exemplary embodiment.

In operation S1110, the wearable device 400 may determine an initial mounting location of the wearable device 400 on the user's head.

In an exemplary embodiment, the wearable device 400 may output an ultrasound signal for arousing the user to a certain somatic sense, receive feedback regarding whether the user has detected the certain somatic sense, or determine how much nerves in the user's brain that are related to the certain somatic sense are activated, thereby determining the initial mounting location of the wearable device 400.

In operation S1120, the wearable device 400 may obtain an ultrasound driving signal for evoking a somatic sense corresponding to the somatosensory data of the content by stimulating a certain region of the user's brain.

In operation S1130, the wearable device 400 may determine whether a variation in a mounting location of the wearable device 400 on the user's head is greater than a certain threshold value.

In operation S1140, when it is determined that the variation in the mounting location of the wearable device 400 is greater than the certain threshold value, the wearable device 400 may output an alarm for guiding the wearable device 400 to the mounting location thereof.

In an exemplary embodiment, the wearable device 400 may output at least one of a sound alarm and a visual alarm for guiding the wearable device 400 to the mounting location thereof.

In an exemplary embodiment, when it is determined that the variation in the mounting location of the wearable device 400 is greater than the certain threshold value, the wearable device 400 may stop outputting the ultrasound signal for evoking the somatic sense corresponding to the somatosensory data.

In operation S1150, when it is determined that the variation in the mounting location of the wearable device 400 is not greater than the certain threshold value, the wearable device 400 may output an ultrasound signal for evoking the somatic sense corresponding to the somatosensory data based on the obtained ultrasound driving signal.

Figure 12:
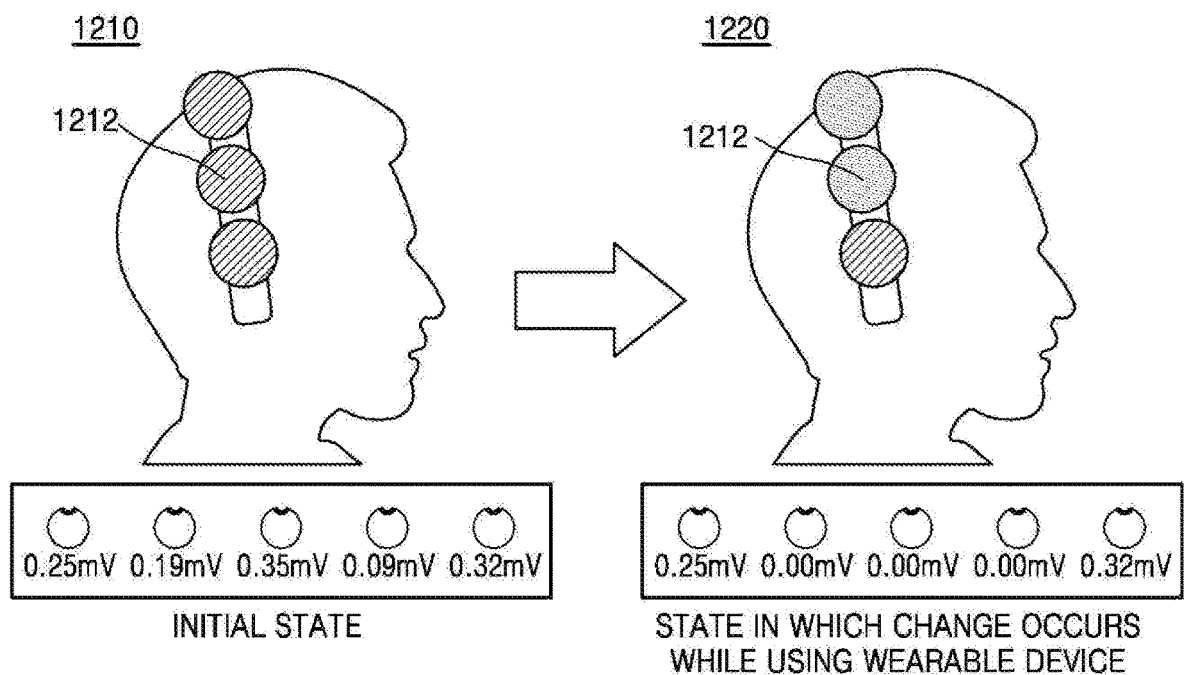
FIG. 12 is a diagram for explaining a method of determining a variation in mounting location of the wearable device, according to an exemplary embodiment.

FIG. 12 is a diagram for explaining a method of determining variations in the mounting location of the wearable device 400, according to an exemplary embodiment.

When the wearable device 400 is placed on the user's head, the wearable device 400 may include a capacitive sensor 1212 at a portion contacting a user's scalp. The capacitive sensor 1212 may output, as a voltage value, a difference between capacitances according to proximity to a human body. The wearable device 400 may determine a change of the mounting location of the wearable device 400, based on the voltage value that is obtained by the capacitive sensor 1212.

Referring to FIG. 12, the voltage value obtained by the capacitive sensor may be obtained in an initial state in which the wearable device 400 is placed at the initial mounting location. The wearable device 400 may include multiple capacitive sensors 1212 and may obtain voltage values respectively from the capacitive sensors.

The wearable device 400 may continuously obtain the voltage values detected by the capacitive sensors 1212 and may monitor whether the mounting location of the wearable device 400 is changed.

Based on the voltage value obtained by the capacitive sensor 1212 in the initial state 1210, the wearable device 400 may determine, as a state 1220 in which a change occurs while using the wearable device 400, a case where a variation in the voltage values obtained by the capacitive sensor 1212 is greater than a certain threshold value.

In an exemplary embodiment, it is determined that the change occurs while using the wearable device 400, the wearable device 400 may output an alarm for guiding the wearable device 400 to the mounting location thereof or stop outputting the ultrasound signal so that an accident, which may occur due to an output of the ultrasound signal to other regions instead of a target area, may be prevented in advance.

Figure 13:
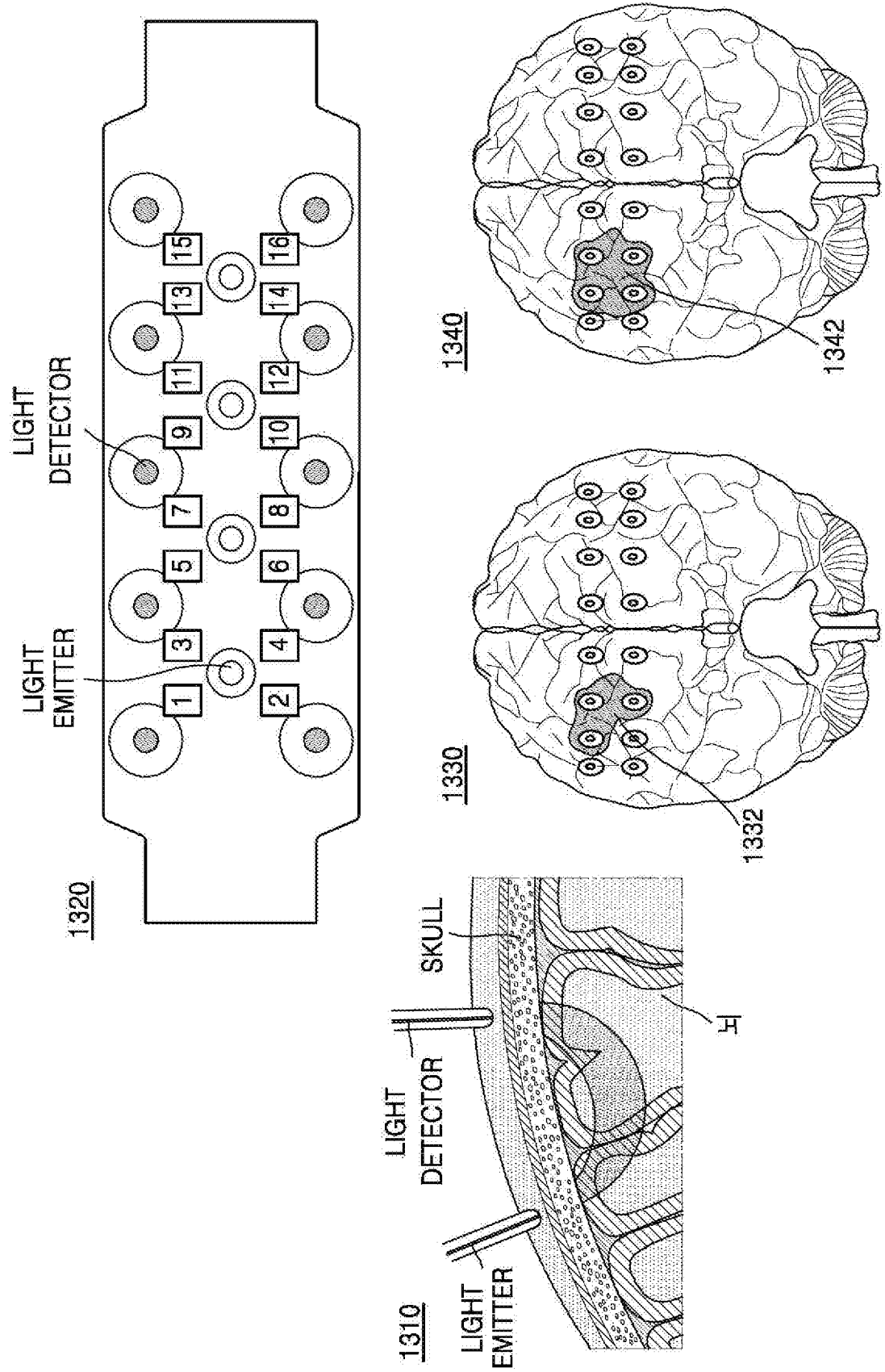
FIG. 13 is a diagram for explaining a method of determining an initial mounting location of the wearable device, according to an exemplary embodiment.

FIG. 13 is a diagram for explaining a method of determining an initial location of the wearable device 400, according to an exemplary embodiment.

The wearable device 400 may include a light emitter and a light detector which are placed at regions of the user's head which face a user's scalp.

Referring to 1320 of FIG. 13, structures of the light emitter and the light detector of the wearable device 400 are illustrated. There may be multiple light emitters and light detectors at regions facing the user's scalp. As the wearable device 400 includes multiple light emitters and light detectors, the wearable device 400 may obtain information regarding a neural activity degree in each region.

Referring to 1310 of FIG. 13, the light emitters of the wearable device 400 may irradiate near infrared rays onto a certain region of the user's brain, and the light detectors may receive the near infrared rays reflected from the certain region. The wearable device 400 may obtain oxygen saturation from the certain region of the user's brain based on an amount of reflected near infrared rays that is obtained by the light detectors. The wearable device 400 may determine the neural activity degree in the certain region of the brain based on an oxygen saturation change in the certain region of the brain.

1330 and 1340 of FIG. 13 respectively illustrate regions 1332 and 1342 of the user's brain when different types of somatic senses are aroused in the user. In the regions 1332 and 1342, the nerves are differently activated based on the oxygen saturation obtained by the light detector.

Respective regions of the brain are responsible for different body parts and senses. Thus, when a certain somatic sense is aroused in the user, a region where nerves are activated may differ according to a body part where the certain somatic sense is evoked, a type of the somatic sense, etc. Based on this fact, the wearable device 400 may output ultrasound signals for arousing the user's brain to certain somatic senses and obtain information regarding how much the nerves are activated in regions of the user's brain which are related to the somatic senses, thereby determining an initial mounting location of the wearable device 400.

The 'initial mounting location' of the wearable device 400 may be a location on the user's head where the wearable device 400 is placed in such a manner that an ultrasound signal for evoking a certain somatic sense is accurately output to a certain region of the user's brain.

Figure 14:
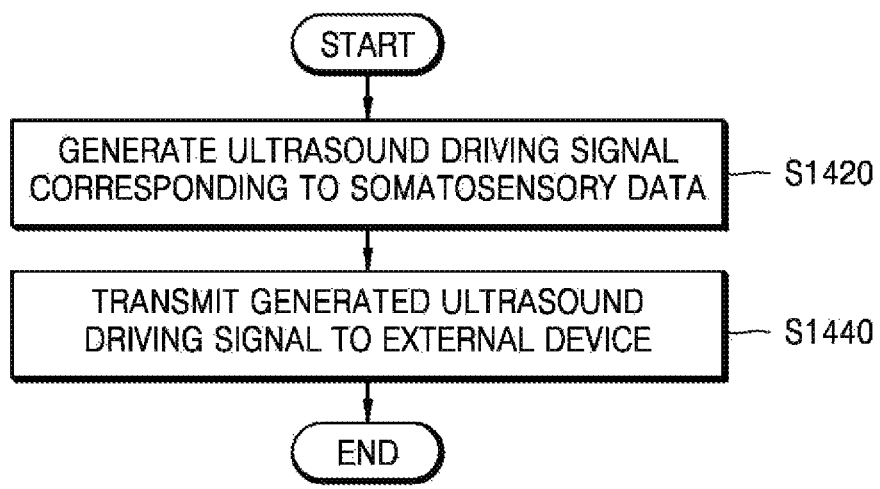
FIG. 14 is a flowchart of a method of providing somatic senses corresponding to content, according to an exemplary embodiment.

FIG. 14 is a flowchart of a method of providing somatic senses corresponding to content, according to an exemplary embodiment.

The method of FIG. 14 may be performed by at least one of the electronic device 10 and the electronic device 300 according to the above embodiments.

In operation S1420, the electronic device 300 may stimulate a certain region of the user's brain and thus may generate an ultrasound driving signal for evoking somatic senses corresponding to somatosensory data.

In an exemplary embodiment, the somatosensory data may correspond to content.

In operation S1440, the electronic device 300 may transmit the generated ultrasound driving signal to an external device.

Figure 15:
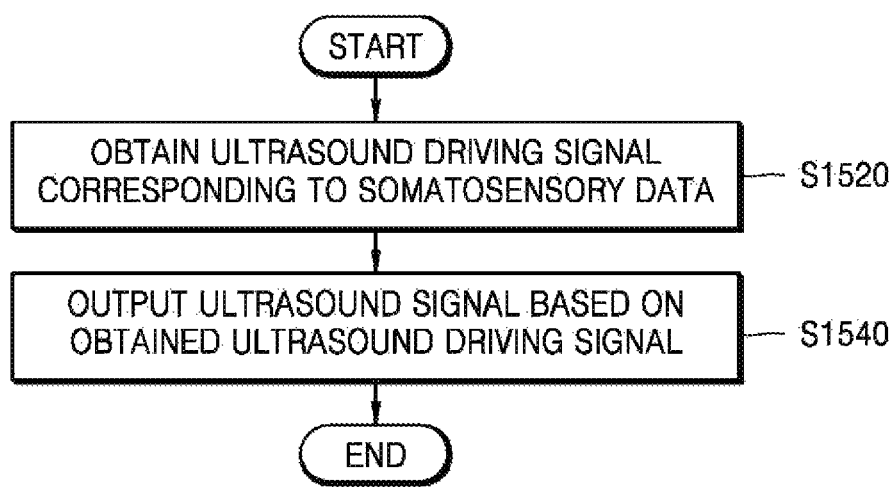
FIG. 15 is a flowchart of a method of providing somatic senses corresponding to content, according to another exemplary embodiment.

FIG. 15 is a flowchart of a method of providing somatic senses corresponding to content, according to another exemplary embodiment.

The method of FIG. 15 may be performed by the wearable device 400 according to the above embodiment.

In operation S1520, the wearable device 400 may stimulate a certain region of the user's brain and thus may obtain an ultrasound driving signal for evoking somatic senses corresponding to somatosensory data.

In an exemplary embodiment, the somatosensory data may correspond to content.

In operation S1540, the wearable device 400 may output an ultrasound signal to the user's brain based on the obtained ultrasound driving signal.

Figure 16:
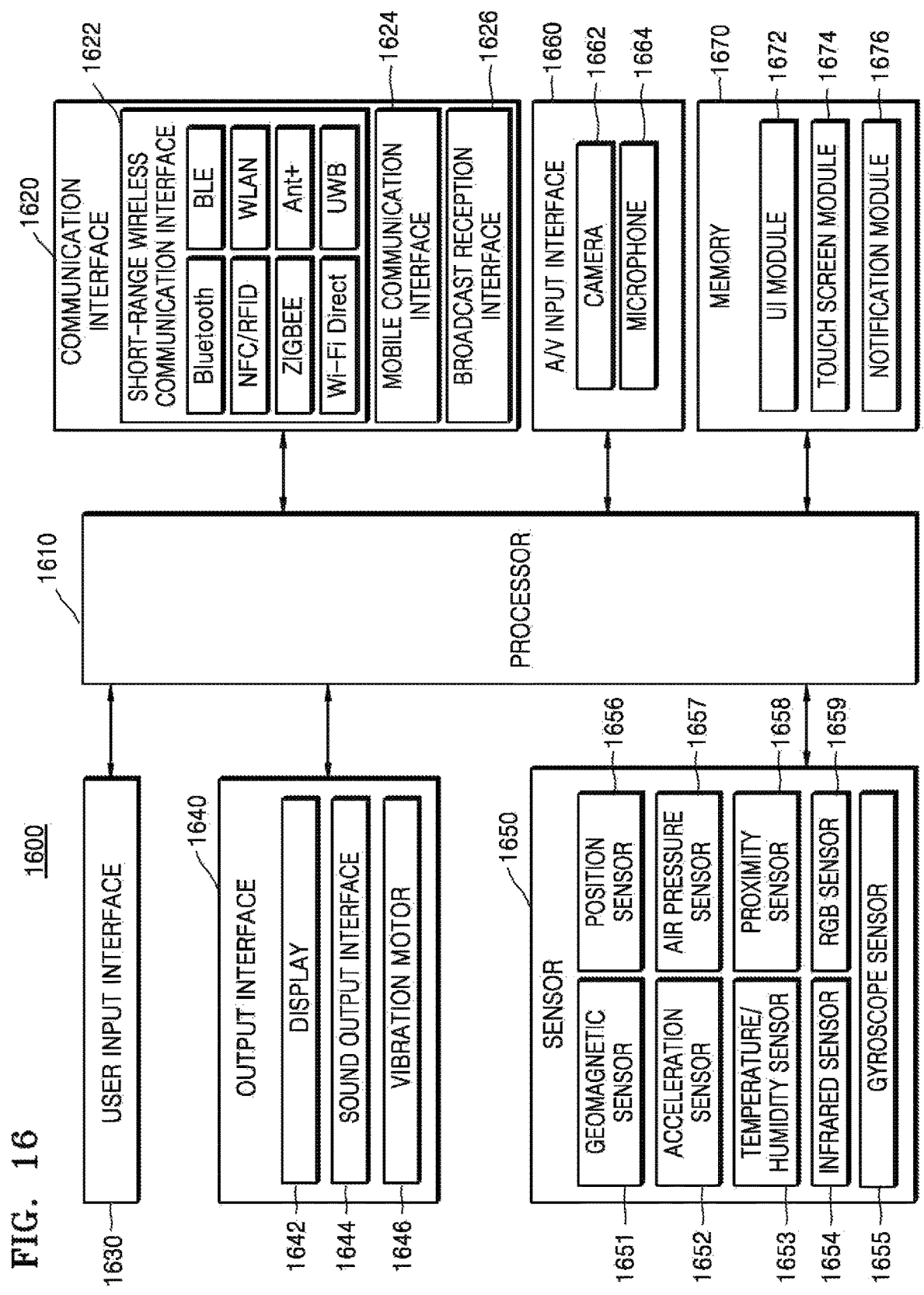
FIG. 16 is a block diagram of an electronic device according to an exemplary embodiment.

FIG. 16 is a block diagram of an electronic device 1600 according to an exemplary embodiment.

As illustrated in FIG. 16, the electronic device 1600 may include a user input interface 1630, an output interface 1640, a processor 1610, a communication interface 1620, a sensor 1650, an Audio/Video (A/V) input interface 1660, and a memory 1670. However, not all of the components of FIG. 16 are necessary for the electronic device 1600. The electronic device 1600 may be implemented by more or less components than the components of FIG. 16.

The user input interface 1630 may be a unit by which a user inputs data so as to control the electronic device 1600. For example, the user input interface 1630 may include a key pad, a dome switch, a touch pad (a touch capacitive-type touch pad, a pressure resistive-type touch pad, an infrared beam sensing-type touch pad, a surface acoustic wave-type touch pad, an integral strain gauge-type touch pad, a Piezo-electric effect-type touch pad, or the like), a jog wheel, a jog switch, or the like. However, the present disclosure is not limited thereto.

The output interface 1640 may output an audio signal, a video signal, or a vibration signal and may include a display 1642, a sound output interface 1644, and a vibration motor 1646.

The display 1642 displays and outputs information that is processed by the electronic device 1600. For example, the display 1642 may output content that is being played or output a user interface for setting a method of providing content-based somatic senses.

When the display 1642 and a touch pad form a layer structure and then are formed as a touch screen, the display 1642 may be used as both an output device and an input device. The display 1642 may include at least one of a liquid crystal display (LCD), a thin film transistor-liquid crystal display (TFT-LCD), an organic light-emitting display device, a flexible display, a 3-dimensional (3D) display, and an electrophoretic display. Also, according to a type of the electronic device 1600, the electronic device 1600 may include at least two displays 1642. In this case, the at least two displays 1642 may face each other by using a hinge.

The sound output interface 1644 may output audio data that is received from the communication interface 1620 or is stored in the memory 1670. The sound output interface 1644 may also output a sound signal (e.g., a call signal receiving sound, a message receiving sound, an alarm sound, or the like) regarding functions performed by the electronic device 1600. The sound output interface 1644 may include a speaker, a buzzer, or the like.

The vibration motor 1646 may output a vibration signal. For example, the vibration motor 1646 may output the vibration signal that corresponds to an output of the audio data (e.g., a call signal receiving sound, a message receiving sound, or the like) or video data. Also, when a touch is input to the touch screen, the vibration motor 1646 may output a vibration signal.

The processor 1610 may generally control all operations of the electronic device 1600. For example, the processor 1610 may generally control the user input interface 1630, the output interface 1640, the sensor 1650, the communication interface 1620, the A/V input interface 1660, and the like by executing the programs stored in the memory 1670.

The sensor 1650 may detect a state of the electronic device 1600 or a state near the electronic device 1600 and may transmit the detected state to the processor 1610.

The sensor 1650 may include at least one of a magnetic sensor 1651, an acceleration sensor 1652, a temperature/humidity sensor 1653, an infrared sensor 1654, a gyroscope sensor 1655, a position sensor (e.g., a global positioning system (GPS)) 1656, an air pressure sensor 1657, a proximity sensor 1658, and an RGB sensor (i.e., an illumination sensor) 1659.

However, the sensor 1650 is not limited thereto. Functions of respective sensors may be intuitively inferred by one of ordinary skill in the art, and thus detailed descriptions thereof will be omitted.

The communication interface 1620 may include at least one component that enables communication between the electronic device 1600 and the external device 20 or communication between the electronic device 1600 and a server (not shown). For example, the communication interface 1620 may include a short-range wireless communication interface 1622, a mobile communication interface 1624, and a broadcast reception interface 1626.

The short-range wireless communication interface 1622 may include a Bluetooth communication interface, a Bluetooth Low Energy (BLE) communication interface, a Near Field communication interface, a WLAN (Wi-Fi) communication interface, a ZigBee communication interface, an infrared Data Association (IrDA) communication interface, a Wi-Fi Direct (WFD) communication interface, an ultra wideband (UWB) communication interface, an Ant+ communication interface, or the like. However, the short-range wireless communication interface 1622 is not limited thereto.

The mobile communication interface 1624 may receive/transmit a wireless signal from/to at least one of a broadcast station, an external terminal, and a server via a mobile communication network. The wireless signal may include various types of data according to reception/transmission of a voice call signal, a video-call call signal, or a text message/multimedia message.

The broadcast reception interface 1626 may receive information regarding a broadcasting signal and/or a broadcast from the outside via a broadcast channel. The broadcast channel may include a satellite channel and a terrestrial channel. Depending on an implementation example, the electronic device 1600 may include the broadcast receiver 1626.

Also, the communication interface 1620 may receive/transmit at least one of somatosensory data corresponding to certain content and an ultrasound driving signal corresponding to the somatosensory data from/to the external device 20 or the server (not shown).

The A/V input interface 1660 may be configured to receive an audio signal or a video signal and may include a camera 1662, a microphone 1664, and the like. The camera 1662 may obtain an image frame such as a static image or a moving image via an image sensor in a video call mode or a shooting mode. An image captured by the image sensor may be processed by the processor 1610 or a separate image processor (not shown).

The image frame processed by the camera 1662 may be stored in the memory 1670 or transmitted to the outside by the communication interface 1620. There may be at least two cameras 1662 according to a structure of a terminal.

The microphone 1664 may receive an external sound signal and process the received external sound signal into electrical voice data. For example, the microphone 1664 may receive a sound signal from an external device or a speaker. The microphone 1664 may use various noise removal algorithms for removing noise generated while the external sound signal is input.

The memory 1670 may store programs for processing and controlling the processor 1610 and may store data that is input to the electronic device 1600 or output therefrom.

The memory 1670 may include at least one storage medium from among a flash memory-type storage medium, a hard disk-type storage medium, a multimedia card micro-type storage medium, card-type memory (e.g., an SD card, an XD memory, or the like), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, a magnetic disc, and an optical disc.

Programs stored in the memory 1670 may be classified into multiple modules according to functions thereof. For example, the programs may be classified into a UI module 1672, a touch screen module 1674, a notification module 1676, and the like.

The UI module 1672 may provide a specialized UI or GUI which interoperates with the electronic device 1600 according to applications. The touch screen module 1674 may detect a user's touch gesture on the touch screen and may transmit information related to the touch gesture to the processor 1610. The touch screen module 1674 according to some embodiments may recognize and analyze touch codes. The touch screen module 1674 may be embodied as separate hardware including a controller.

Various sensors may be arranged in or near the touch screen so as to detect a touch or a proximate touch on the touch sensor. An example of the sensor to detect the touch on the touch screen may be a tactile sensor. The tactile sensor detects a contact of a specific object by at least as much as a person can detect. The tactile sensor may detect various types of information such as the roughness of a contact surface, the hardness of the contact object, a temperature of a contact point, or the like.

The proximity sensor indicates a sensor of detecting existence of a subject that comes close to or in vicinity of a certain detection surface by using an electromagnetic field or infrared rays instead of mechanical contact. Examples of the proximity sensor may be a through-scan type photoelectric sensor, a diffused reflection-type photoelectric sensor, a mirror reflection-type photoelectric sensor, a high-frequency oscillation-type proximity sensor, a capacitive proximity sensor, an infrared proximity sensor, and the like. The touch gesture of the user may include a tap gesture, a touch & hold gesture, a double tap gesture, a drag gesture, a panning gesture, a flick gesture, a drag & drop gesture, a swipe gesture, or the like.

The notification module 1676 may generate a signal for notifying the occurrence of events on the electronic device 1600. Examples of events occurring on the electronic device 1600 may be call signal reception, message reception, a key signal reception, a schedule notification, and the like. The notification module 1676 may output a notification signal as a video signal through the display 1642, as an audio signal through the sound output interface 1644, or as a vibration signal through the vibration motor 1646.

The one or more embodiments may be written as programs executable by a computer and may be implemented in a general-use digital computers that execute the above programs using a computer-readable recording medium. Also, structures of data used in the above embodiments may be recorded by computer-readable recording media. Also, structures of data used in the above embodiments may be recorded on the computer-readable recording medium in various manners. The above embodiments may be implemented as recording media including instructions, e.g., program modules, which is executable by a computer. When software modules or algorithms are involved, these software modules may be stored as program instructions or computer-readable code executable on a processor on a computer-readable recording medium. The computer-readable recording medium may be an arbitrary recording medium that may be accessed by a computer and may include a volatile or non-volatile medium and a removable or non-removable medium. Examples of the computer-readable recording medium include magnetic storage media (e.g., ROM, floppy disks, hard disks, etc.), optical recording media (e.g., CD-ROMs, or DVDs), etc., but the computer-readable recording medium is not limited thereto. In addition, the computer-readable recording medium may include a computer storage medium and a communication medium.

The computer-readable recording media can also be distributed over network-coupled computer systems, and data, e.g., program instructions and code, which is stored in the distributed media may be executed by at least one computer.

The embodiments of the present disclosure can be written as computer programs and can be implemented in general-use digital computers that execute the programs using a computer-readable recording medium. Also, the data structures used in the embodiments may be written to the computer-readable recording medium through various media. Moreover, the embodiments may be realized as a recording medium, e.g., a program module, It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An electronic device for providing somatic senses based on content, the electronic device comprising:
   a communication interface;
   a user interface; and
   a processor configured to:
   generate an ultrasound driving signal for evoking somatic senses corresponding to somatosensory data by stimulating a certain region of the brain of a user,
   control the communication interface to transmit the generated ultrasound driving signal to an external device, the somatosensory data corresponding to the content,
   correct a timing to drive the ultrasound driving signal based on a delay time taken for sound pressure of an ultrasound wave of an ultrasound signal output by the ultrasound driving signal to stimulate the brain and a delay time taken for the user to recognize somatic sense evoked by simulating the brain
   control the user interface to display a first item of a sense filtering and a second item of a sense augmentation setting,
   based on a first input on the first item of the sense filtering being received, generate the ultrasound driving signal for evoking somatic senses in which a somatic sense corresponding to the first input is removed, and
   based on a second input on the second item of the sense augmentation setting being received, generate the ultrasound driving signal for evoking somatic senses in which a somatic sense corresponding to the second input is augmented.

2. The electronic device of claim 1, wherein the content comprises somatosensory elements, and
   the somatosensory data comprises at least one of types of somatic senses, locations where the somatic senses are evoked, points in time when the somatic senses are evoked, intensities of the somatic senses, and frequencies of the somatic senses corresponding to the somatosensory elements, the somatosensory data being synchronized with the somatosensory elements of the content.

3. The electronic device of claim 1, wherein the content comprises somatosensory elements, and
the processor is further configured to generate the somatosensory data by analyzing the somatosensory elements.

4. The electronic device of claim 1, wherein the content comprises somatosensory elements,
the electronic device further comprises a user input interface configured to receive an input of generating the somatosensory data corresponding to the somatosensory elements, and
the processor is further configured to generate the somatosensory data based on the input received by the user input interface.

5. The electronic device of claim 1, wherein the processor is further configured to generate the ultrasound driving signal based on the somatosensory data and content feature information indicating features of the content, the features comprising at least one of a content type, brightness of a screen to which the content is output, and volume of output audio of the content.

6. The electronic device of claim 1, wherein the processor is further configured to generate the ultrasound driving signal based on the somatosensory data and user characteristic information indicating characteristics of the user, the characteristics comprising at least one of a threshold value regarding a certain stimulus to the user, a recognition time, preference for a certain somatic sense, and age of the user.

7. A wearable device for providing somatic senses based on content, the wearable device comprising:
an ultrasound transducer;
a user interface; and
a processor configured to:
obtain an ultrasound driving signal for evoking somatic senses corresponding to somatosensory data by stimulating a certain region of the brain of a user, and
control the ultrasound transducer to output an ultrasound signal based on the obtained ultrasound driving signal,
wherein the somatosensory data corresponds to the content,
wherein a timing to drive the ultrasound driving signal is corrected based on a delay time taken for sound pressure of an ultrasound wave of the ultrasound signal output by the ultrasound driving signal to stimulate the brain and a delay time taken for the user to recognize somatic sense evoked by stimulating the brain, and
wherein the processor is further configured to:
control the user interface to display a first item of a sense filtering and a second item of a sense augmentation setting,
based on a first input on the first item of the sense filtering being received, generate the ultrasound driving signal for evoking somatic senses in which a somatic sense corresponding to the first input is removed, and
based on a second input on the second item of the sense augmentation setting being received, generate the ultrasound driving signal for evoking somatic senses in which a somatic sense corresponding to the second input is augmented.

8. The wearable device of claim 7, wherein the content comprises somatosensory elements, and
the somatosensory data comprises at least one of types of somatic senses, locations where the somatic senses are evoked, points in time when the somatic senses are evoked, intensities of the somatic senses, and frequencies of the somatic senses corresponding to the somatosensory elements, the somatosensory data being synchronized with the somatosensory elements of the content.

9. The wearable device of claim 7, wherein the content comprises somatosensory elements, and
the processor is further configured to analyze the somatosensory elements and generate the somatosensory data.

10. The wearable device of claim 7, wherein the processor is further configured to determine an initial mounting location of the wearable device and determine, based on the determined initial mounting location, whether a variation in a mounting location of the wearable device is greater than a certain threshold value, and
the wearable device further comprises an output interface configured to output at least one of a sound alarm and a visual alarm for guiding the wearable device to the mounting location of the wearable device when the variation is greater than the certain threshold value.

11. A method of providing somatic senses based on content, the method comprising:
generating an ultrasound driving signal for evoking somatic senses corresponding to somatosensory data by stimulating a certain region of the brain of a user;
transmitting the generated ultrasound driving signal to an external device, wherein the somatosensory data corresponds to the content;
correcting a timing to drive the ultrasound driving signal based on a delay time taken for sound pressure of an ultrasound wave of an ultrasound signal output by the ultrasound driving signal to stimulate the brain and a delay time taken for the user to recognize somatic sense evoked by stimulating the brain;
displaying a first item of a sense filtering and a second item of a sense augmentation setting;
based on a first input on the first item of the sense filtering being received, generating the ultrasound driving signal for evoking somatic senses in which a somatic sense corresponding to the first input is removed; and
based on a second input on the second item of the sense augmentation setting being received, generating the ultrasound driving signal for evoking somatic senses in which a somatic sense corresponding to the second input is augmented.

12. The method of claim 11, wherein the content comprises somatosensory elements, and
the somatosensory data comprises at least one of types of somatic senses, locations where the somatic senses are evoked, points in time when the somatic senses are evoked, intensities of the somatic senses, and frequencies of the somatic senses corresponding to the somatosensory elements, the somatosensory data being synchronized with the somatosensory elements of the content.

13. The method of claim 11, wherein the content comprises somatosensory elements, and
the method further comprises generating the somatosensory data by analyzing the somatosensory elements.

14. The method of claim 11, wherein the content comprises somatosensory elements, and
the method further comprises:
receiving a user input for generating the somatosensory data corresponding to the somatosensory elements; and
generating the somatosensory data based on the received user input.

15. The method of claim 11, wherein the generating of the ultrasound driving signal is performed based on the somatosensory data and content feature information indicating features of the content, the features comprising at least one of a content type, brightness of a screen to which the content is output, and volume of output audio of the content.

16. The method of claim 11, wherein the generating of the ultrasound driving signal is performed based on the somatosensory data and user characteristic information indicating characteristics of the user, the characteristics comprising at least one of a threshold value regarding a certain stimulus to the user, a recognition time, preference for a certain somatic sense, and age of the user.

17. A non-transitory computer-readable recording medium having recorded thereon a program which, when executed by a computer, performs the method of claim 11.

\* \* \* \* \*